(12) United States Patent
Ehrenreich

(10) Patent No.: US 9,180,165 B2
(45) Date of Patent: *Nov. 10, 2015

(54) USE OF EPO RECEPTOR ACTIVATION OR STIMULATION FOR THE IMPROVEMENT OF THE EDSS SCORE IN PATIENTS WITH MULTIPLE SCLEROSIS

(76) Inventor: Hannelore Ehrenreich, Göttingen (DE)

( * ) Notice: Subject to any disclaimer, the term of this patent is extended or adjusted under 35 U.S.C. 154(b) by 445 days.

This patent is subject to a terminal disclaimer.

(21) Appl. No.: 12/136,509

(22) Filed: Jun. 10, 2008

(65) Prior Publication Data

US 2009/0022734 A1 Jan. 22, 2009

(30) Foreign Application Priority Data

Jul. 19, 2007 (EP) .................... 07014225

(51) Int. Cl.
*A61K 38/00* (2006.01)
*A61K 38/19* (2006.01)
*A61K 38/18* (2006.01)

(52) U.S. Cl.
CPC ................ *A61K 38/1816* (2013.01)

(58) Field of Classification Search
None
See application file for complete search history.

(56) References Cited

U.S. PATENT DOCUMENTS

| | | | |
|---|---|---|---|
| 5,441,868 A | 8/1995 | Lin | |
| 5,994,127 A | 11/1999 | Selden et al. | |
| 6,638,768 B1 | 10/2003 | Le Mouellic et al. | |

FOREIGN PATENT DOCUMENTS

| | | |
|---|---|---|
| DE | 10 2006 004 008 A1 | 8/2007 |
| EP | 1295604 A | 3/2003 |
| WO | WO 85/02610 A1 | 6/1985 |
| WO | WO 86/03520 A1 | 6/1986 |
| WO | WO 90/11354 A1 | 10/1990 |
| WO | WO 91/06667 A1 | 5/1991 |
| WO | WO 91/09955 A1 | 7/1991 |
| WO | WO 93/09222 A2 | 5/1993 |
| WO | WO 94/12650 A2 | 6/1994 |
| WO | WO 95/05465 A1 | 2/1995 |
| WO | WO 95/31560 A1 | 11/1995 |
| WO | WO 00/61164 A1 | 10/2000 |
| WO | WO 2007/085453 A1 | 8/2007 |

OTHER PUBLICATIONS

Savino et al. Jour Neuroimmunol 172: 27-37, 2006.*
Pokryszko-Dragan et al. (Pol Merkur Lekarski 19: 654-658, 2005)—abstract only.*
Bitonti et al. PNAS 101: 9763-9768, 2004.*
Oliveri et al. (Neurology 50: 1833-1836, 1998).*
Complete Epoetin Alfa information <http://www.drugs.com/ppa/epoetin-alfa-erythropoietin-epo.html> downloaded on Mar. 8, 2014.*
Complete methylprednisolone information <http://www.drugs.com/ppa/methylprednisolone.html> downloaded on Mar. 8, 2014.*
Kurtzke. (Ann Neurol 36 Suppl: S73-9, 1994—abstract only).*
Agnello et al., *Brain Research*, 952: 128-134 (2002).
Banks et al., *European Journal of Pharmacology*, 505: 93-101 (2004).
Brines et al., *PNAS*, 97(19): 10526-10531 (2000).
Brines et al., *Neuroscience*, 6: 484-494 (Jun. 2005).
Cutter et al., *Brain*, 122: 871-882 (1999).
Ehrenreich et al., *Molecular Psychiatry*, 9: 42-54 (2004).
Eschbach et al., *The New England Journal of Medicine*, 3: 73-78 (Jan. 1987).
Fahn, "Unified Parkinson's Disease Rating Scale," NJ: Macmillan Health Care Information (1987).
Goetz et al., *Movement Disorders*, 18(7): 738-750 (2003).
Huber, Tewes U. Hamburg-Wechsler Intelligenztest fur Erwachsene, Bern (1991).
Koller, *Neurology*, 42 (Suppl 4): 27-31 (Apr. 1992).
Kongs et al., "Wisconsin Card Sorting Test—64 Card Version," Psychological Assessment Resources, Inc., Odessa, Florida (2000).
Kurtzke, *Neurology*, 33: 1444-1452 (1983).
Kwack et al., *Seminars in Dialysis*, 19(2): 146-151 (Mar.-Apr. 2006).
Lehrl, Mehrfachwahl-Wortschatz-Intelligentztest. MWT-B, Spitta Verlag GmbH, Germany (1999).
Leist et al., *Science*, 305: 239-242 (2004).
Lynch et al., *Cellular and Molecular Biology*, 46(4): 865-869 (2000).
MacQuarrie, *The Journal of Personnel Research*, V(9): 329-337 (1927).
*Neurology*, 42 (Suppl 4): 41-48 (Apr. 1992).
Randolph, "Repeatable Battey for the Assessment of Neurophychological Status," Psychological Corporation, Harcourt, Texas (1998).
Reitan, *Perceptual and Motor Skills*, 8: 271-276 (1958).
Rudick et al., *Neurology*, 56: 1324-1330 (May 2001).
Sfagos et al., *Multiple Sclerosis*, 11: 272-275 (2005).
Wechsler, Administration and Scoring Manual, The Psycological Corporation, Harcourt, Texas (1998).
Xenocostas et al., *Eur. J. Clin. Pharmacol.*, 61: 189-195 (2005).
Zimmermann et al., Testbatterie zur Aufmerksamkeitsprufung (TAP), Psytest, Germany (1993).
Savino et al., "Delayed administration of erythropoietin and its non-erythropoietic derivatives ameliorates chronic murine autoimmune encephalomyelitis," *Journal of NeuroImmunology*, vol. 172, No. 1-2, pp. 27-37 (Mar. 1, 2006).
Sirén et al., "Therapeutic Potential of Erythropoietin and its Structural or Functional Variants in the Nervous System," *Neurotherapeutics: The Journal of the American Society for Experimental NeuroTherapeutics*, vol. 6, pp. 108-127 (2009).

* cited by examiner

*Primary Examiner* — Daniel E Kolker
*Assistant Examiner* — Aditi Dutt
(74) *Attorney, Agent, or Firm* — Leydig, Voit & Mayer, Ltd.

(57) ABSTRACT

The invention provides a method of improving the expanded disability status scale (EDSS) score achieved by mammals affected by multiple sclerosis, in which a substance effecting increased and/or prolonged activation and/or stimulation of the erythropoietin (EPO) receptor is administered to the mammal. In certain embodiments, the substance is administered in intervals which are interrupted by application-free periods of time in which said substance is not administered.

31 Claims, 5 Drawing Sheets

Figure 1:
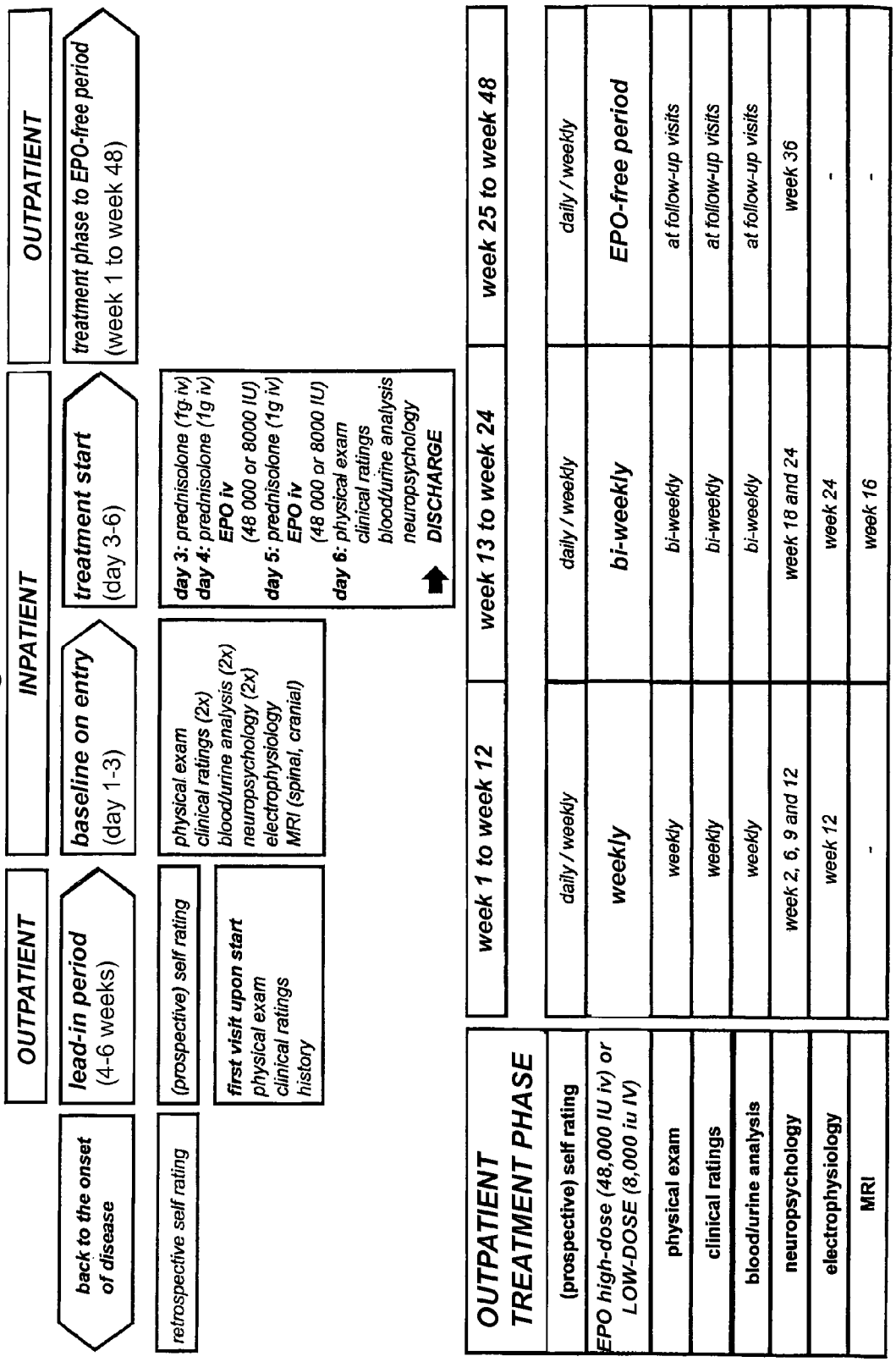

Figure 4
a MacQuarrie Tapping
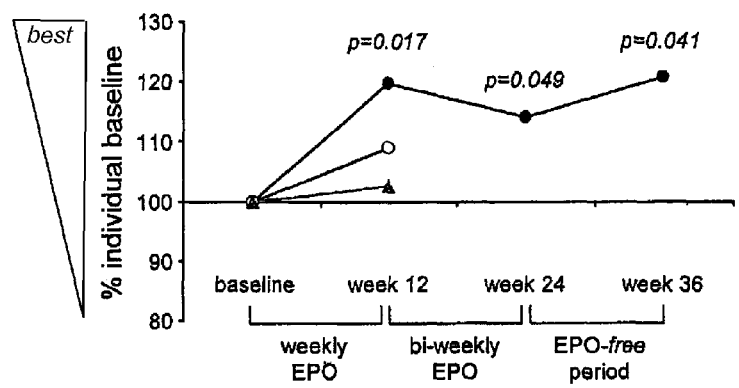
b MacQuarrie Dotting
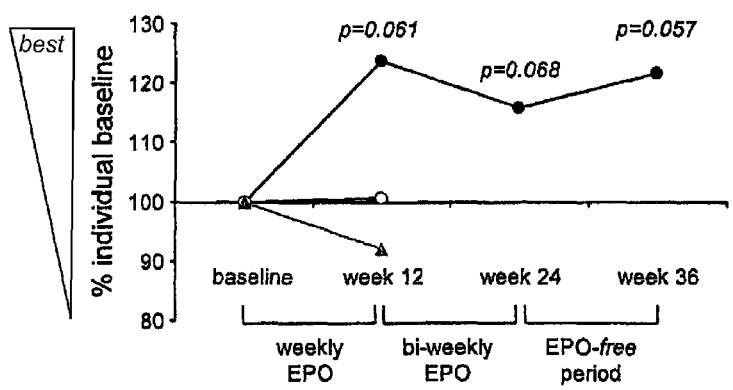
c 9-Hole Peg Test *(non-dominant hand)*
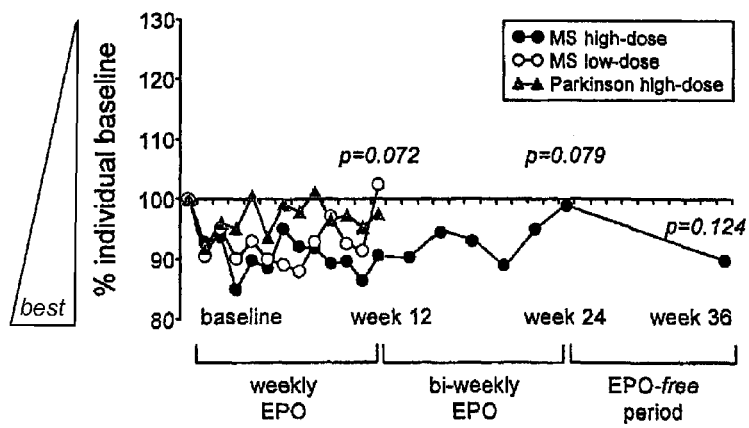

USE OF EPO RECEPTOR ACTIVATION OR STIMULATION FOR THE IMPROVEMENT OF THE EDSS SCORE IN PATIENTS WITH MULTIPLE SCLEROSIS

This application claims priority to European patent application no. 07 014 225.2, filed on Jul. 19, 2007, which is incorporated herein by reference.

The present invention relates to a method for the improvement of the EDSS score achieved by mammals which are affected by multiple sclerosis and also the use of substances effecting increased and/or prolonged activation and/or stimulation of the erythropoietin receptor for this purpose and also for the production of a drug for this purpose.

With approx. 80 to 110 cases of multiple sclerosis (MS) per 100,000 persons, multiple sclerosis is the most frequent chronic disease of the central nervous system. A third of patients thereby shows a primary or secondary progressive course of the multiple sclerosis, for which no therapy has been available to date. Understanding and treatment of the progressive phase of multiple sclerosis (MS), which is characterized by the steady accumulation of neurological disability, is far from being satisfactory. Progression is most likely driven by the high prevalence of neurodegenerative compared with inflammatory pathological changes, explaining the limited long-term efficacy of current anti-inflammatory and immunosuppressive treatment strategies. It seems that once the cascade of events leading to neuronal and axonal loss is established, even an effective suppression of inflammation fails to protect from clinical disease progression. The development of add-on treatments targeting axonal repair and remyelination and/or the slowing of disease progression through neuroprotection/neuroregeneration remains therefore the most important challenge and goal in clinical management of chronic progressive MS.

Disability of patients affected by multiple sclerosis can be determined based on different parameters. One of the parameters—mainly determining motoric ability—is the Expanded Disability Status Scale (EDSS). This parameter is described in Kurtzke J. F., Rating neurologic impairment in multiple sclerosis: an expanded disability status scale (EDSS), Neurology 1983; 33: 1444-52. At present, no therapy is available which would improve the EDSS score achieved by patients.

In the following and throughout this application, the term "achieved by patients" shall have the same or corresponding meaning as "achievable by patients".

Erythropoietin (EPO) is a glycoprotein produced naturally in the body, having a molecular weight of 34,000 D. It is an essential growth factor for the production of erythrocytes and was isolated for the first time in 1977. It binds to and stimulates the endogenous erythropoietin receptor.

Erythropoietin has been in frequent clinical use for many years in patients with renal anaemia, in the case of nephrodialysis, in order to obtain fairly large quantities of autologous blood before planned operations, and it also appeared in press headlines as a doping agent.

Erythropoietin thereby proved to be exceptionally well tolerated with only minor or no side effects at all. Intolerance reactions or anaphylactic reactions are rarities with erythropoietin.

There are a plethora of substances, known and produced, which all are considered to increase or prolong the activation and/or increase or prolong stimulation of the erythropoietin receptor (e.g. as shown in the following paragraph). Besides erythropoietin itself, whether native or recombinant, whether in native sequence or even after sequence changes or sequence shortening, erythropoietin analogues, erythropoietin fragments or erythropoietin agonists were developed. As examples for recombinant erythropoietins, Epoetin α (Epogen by Amgen Inc., Procrit by OrthoBiotech Inc., Johnson and Johnson Inc.), Epoetin β (Neorecormon™ by F. Hoffmann-La Roche AG) and Epoetin ω (Epomax™), Epoetin δ (DynEpo™, Shire Pharmaceuticals Group PLC) with variing glycosilation and sialysation are known. Genetically modified EPO are known as Darbepoetin α™ (by Amgen Inc.) and CERA™ (by F. Hoffmann-La Roche AG). Further, erythropoietin receptor activating antibody (e.g. by Abbott), fusion proteins like Epo-Fc and carbamylated EPO (CEPO™, by H. Lundbeck A/S) are known. Endogenous erythropoietin stimulating substances, substances increasing the release and/or activity of endogenous erythropoietin (e.g. HIF-stabilisers, e.g. by FibroGen Inc. or Torrent Pharmaceuticals Ltd.) are also known. Furthermore, erythropoietin analogues or mimetics are known, e.g. SEP (Synthetic Erythropoiese Protein, by Gryphon Therapeutics), Hematide™ (by Affymax Inc.) and others known as EPO-analogues or EPO-mimetics by AplaGen. It is even known to transfer the gene coding for erythropoietin into a patient in order to express erythropoietin.

All of these substances are known to increase and/or prolong the activation and/or stimulation of the erythropoietin receptor besides their antiapoptotic, tissueprotective effect. Some useable EPO variants are published for example in the following publications:

Leist et al., Science 2004, Vol. 305, pp. 239-242, WO 86/03520, WO 85/02610, WO 90/11354, WO 91/06667, WO 91/09955, WO 93/09222, WO 94/12650, WO 95/31560, WO 95/05465. An overview of known EPO variants, analogues, mimetics and equivalents which can also be used in their entirety in the present invention and also of known fields of use thereof appears in Brines and Cerami, Nature Reviews, Neuroscience, June 2005, Vol. 6, pages 484-494.

WO 00/61164 discloses the use of EPO for the protection of neuronal tissue, in particular also of the central nervous system. It is mentioned in passing in this document that multiple sclerosis might also be treated with EPO.

WO 00/61164 in fact discloses the use of EPO for the treatment of multiple sclerosis but indicates no experimental data or treatment regime at all. It is not disclosed therein, in what respect (cognitive, motoric function or others) patients suffering from multiple sclerosis might benefit from treatment with EPO.

It is therefore the object of the present invention to develop a method for the safe improvement of the expanded disability status scale (EDSS) score achieved by mammals and the use of substances effecting increased and/or prolonged activation and/or stimulation of the erythropoietin receptor for the safe improvement of the expanded disability status scale (EDSS) score achieved by mammals affected by multiple sclerosis.

This object is achieved by the method and also the use of the method as described herein. Advantageous developments of the method according to the invention and of the use according to the invention are also described herein.

According to the invention, in the method of the present invention in mammals, in particular in humans, a substance effecting increased and/or prolonged activation and/or increased and/or prolonged stimulation of the erythropoietin receptor is administered to the mammal, e.g. to a human patient affected by multiple sclerosis.

As substance effecting increased and/or prolonged activation and/or stimulation of the erythropoietin receptor and substance as described above may be used, e.g. erythropoietin, native or recombinant, variants or derivatives of erythropoietin, analogues, mimetics, agonists of erythropoietin or substances for genetically altering the patient in order to achieve said activation/stimulation of the erythropoietin receptor.

The present invention for the first time shows, that a treatment or use according to the present invention improves not only cognitive parameters but effect a significant improvement of the EDSS score in patients suffering from multiple sclerosis. This improvement has not been known before and could not have been foreseen considering the purely speculative nature of the above cited documents generally relating to the use of erythropoietin in treatment of multiple sclerosis. It is of great importance that the proposed method and proposed use is safe with no or only minor side effects.

The method can be used with patents suffering from any kind of multiple sclerosis, e.g. primary progressive multiple sclerosis (PPMS), secondary progressive multiple sclerosis (SPMS), relapsing/remitting multiple sclerosis (RRMS) or progressive relapsing multiple sclerosis (PRMS).

In particular, an improvement in the symptoms was observed not only in the case of chronic-progressive multiple sclerosis but also in the case of relapsing-remitting multiple sclerosis. In particular in the case of (chronic) progressive multiple sclerosis, a deterioration in the symptoms would have been expected during the treatment-free interval. However stabilisation also occurred here.

Advantageously, the erythropoietin is applied intermittently. This means that, as an advantageous development of the present invention, an interval treatment is proposed. It is thereby particularly advantageous if the treatment comprises a sequence of periods of time with application of EPO (application period) and periods of time without application of EPO (application-free periods).

The individual periods of time thereby comprise several weeks. A sequence has emerged as particularly advantageous in which each application period lasts 12 to 48 weeks, advantageously 18 to 36 weeks, advantageously 24 to 28 weeks, whilst the application-free periods last 8 to 53 weeks, advantageously 16 to 28 weeks. Within the application periods, the dosage can be varied, for example firstly a period of time with a weekly application and a subsequent period of time with a two-weekly application.

The dosage is thereby respectively in the values described herein, particularly advantageously in a dosage range of 5,000 IU to 100,000 IU (international units), advantageously in a dosage range of 30.000 IU to 60.000 IU, advantageously in a 5 dosage range of 40000 IU to 50000 IU, per week or per administration, including or excluding the respective range limits. In the alternative, doses equivalent to said doses given in the preceding sentence, which lead to comparable erythropoietin levels or comparable erythropoietin receptor activating or stimulating biological activity may be used as dosage.

With the mentioned interval dosage schemes, the result surprisingly is a constant improvement in the clinical symptoms during treatment. The improved level is maintained astonishingly in the interval and the second cycle produces a further improvement.

The interval treatment according to the invention is an innovative improvement to the entire concept of neuroprotection which, in the case of EPO with multiple sclerosis, exploits in addition the fact that the result with half-yearly erythropoietin treatment is a latent, desired lack of iron. Since lack of iron can be advantageous in addition for the known neuroprotective EPO effect in chronic inflammatory diseases such as multiple sclerosis, advantageously iron is substituted neither in the treatment nor in the treatment-free phase. The treatment-free phase serves therefore also for slow replenishment of the depleted iron stores, as a result of balanced nutrition.

In particular in the case of use of EPO with haematopoietic effect, the neuroprotective effect is consequently supplemented by the latent lack of iron produced by the EPO treatment.

The effect according to the invention is also achieved however already by using EPO derivatives or variants without haematopoietic effect. It turned out, that is not of particular relevance in the present invention whether the EPO analogues or erythropoietin fragments which are used have a haematopoietic effect (e.g. Epogen™) or not (e.g. CEPO™).

The above explanation relates to the method but the invention is not only directed to the therapeutic method but also to the use of the above mentioned substances in a method of this type and also the use of the above mentioned substances for the production/manufacturing of a drug for use in a method of this type.

In the following, an explanatory study is described which provides experimental proof for the invention. This example contains four tables (table 1, supplementary table 1, supplementary table 2, supplementary table 3) as part of the description and is further explained on the basis of 5 figures.

BRIEF DESCRIPTION OF THE SEVERAL VIEWS OF THE DRAWING(S)

Figure 2:
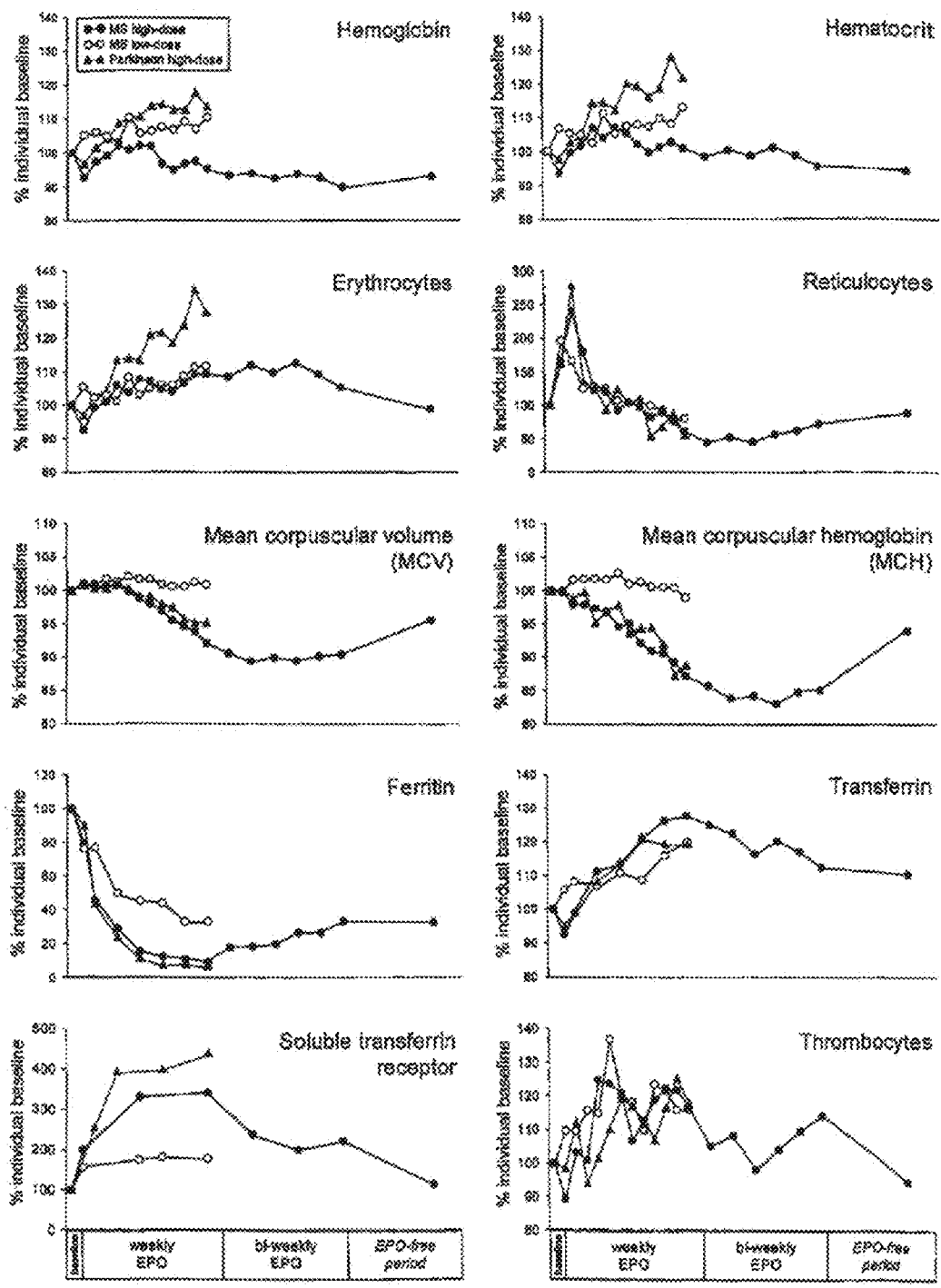
Figure 3:
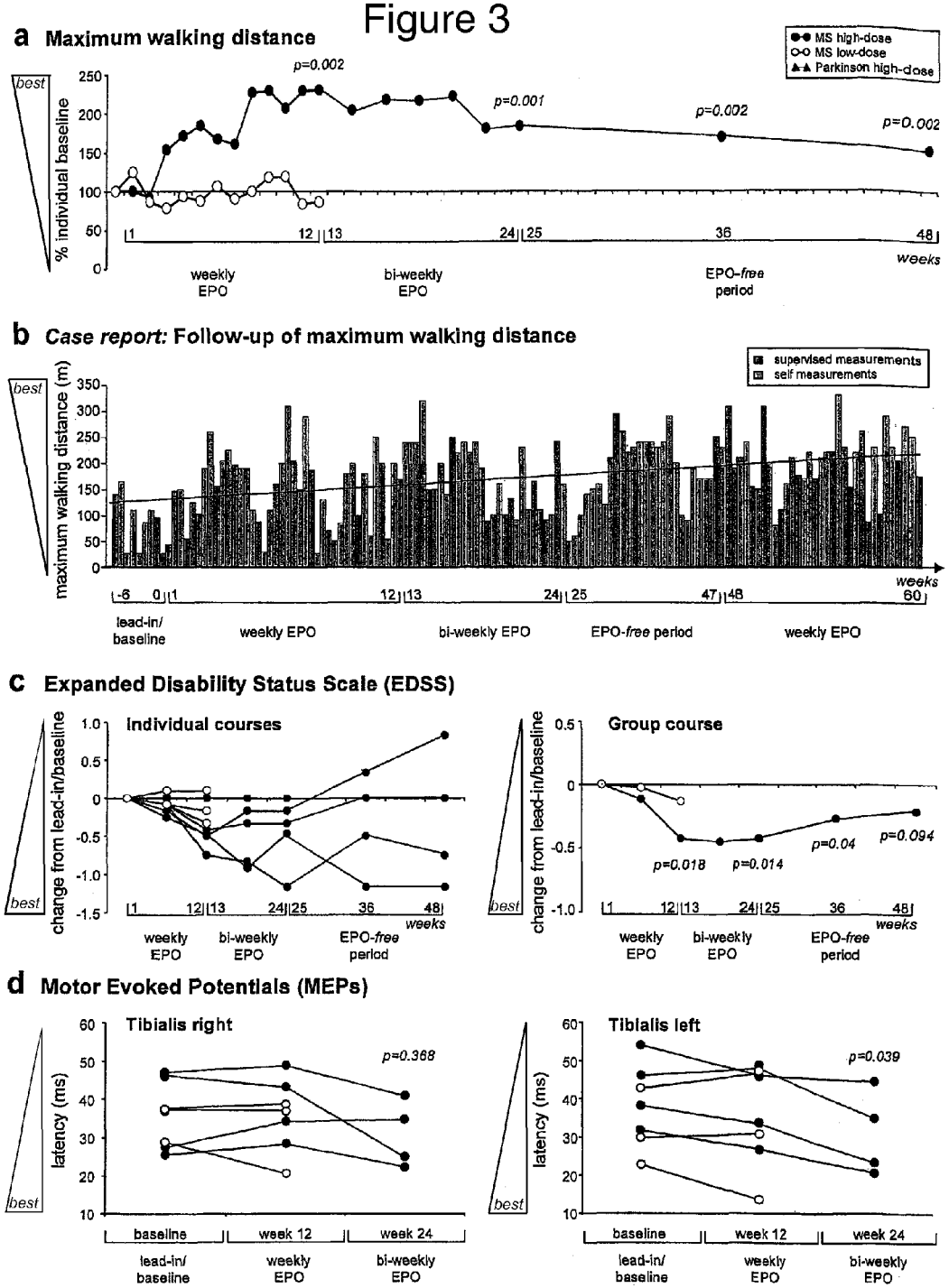

The figures describe the following:

FIG. 1 shows the design of the EPO MS exploratory study. Low-dose EPO treatment was only performed until week 12;

FIG. 2 shows changes in blood cell counts and iron parameters during and after EPO treatment. The mean of two baseline values of each patient was set to 1000% for each of the laboratory parameters and used for calculating individual change over time. Mean change of all patients within each group during follow-up upon treatment or during the treatment-free period is expressed in % baseline. Low-dose EPO MS patients and Parkinson patients were only followed until week 12. Filled circles: high-dose EPO MS patients (N=5); open circles: low-dose EPO MS patients (N=3); gray triangles: high-dose EPO Parkinson patients (N=2);

FIG. 3 shows changes in parameters of motor function upon EPO treatment. (a) The mean of all available baseline values of maximum walking distance of each patient obtained during the whole lead-in period was set to 100% and used for calculating individual change over time. Mean change of all patients within each group during follow-up upon treatment or during the treatment-free period is expressed in % baseline. (b) Follow-up of maximum walking distance of one high-dose EPO MS patient over a total of 60 weeks, including two EPO treatment periods, is presented as raw data for every test time-point. The trend line illustrates the improvement over time. (c) For presenting the course of EDSS scores during the study, mean individual baseline was set to 0 and subsequent values denote change of EDSS score during follow-up of individual MS patients (left panel) or of mean EDSS score of the groups (right panel). For determining individual EDSS change over time, the mean value of consecutive ratings over six week follow-up periods was used. (d) Intra-individual course of central motor conduction time (Tibialis MEP, original data; MS high-dose patients N=4, due to methodological problems in one patient during baseline measurement).

Figure 5:
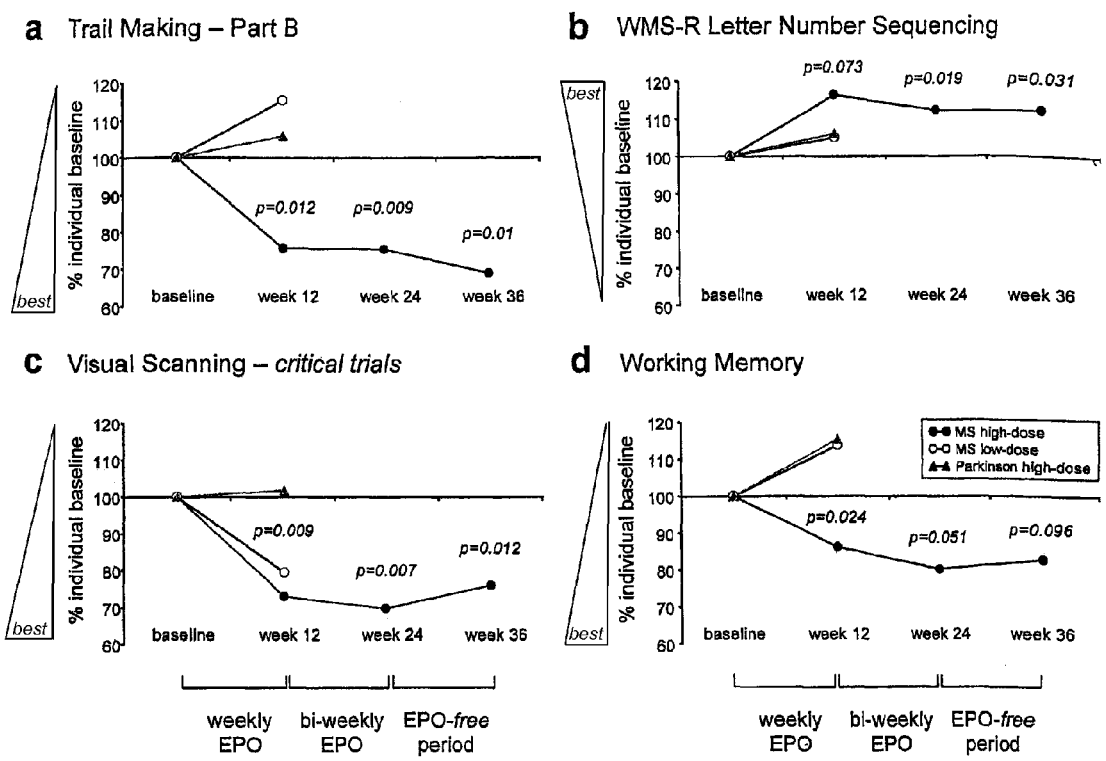

Low-dose EPO MS patients and Parkinson patients were only followed until week 12. Filled circles: high-dose EPO MS patients (N=5); open circles: low-dose EPO MS patients (N=3); gray triangles: high-dose EPO Parkinson patients (N=2). Significance values refer to the high-dose EPO MS patients only and denote changes of the respective parameter from baseline to the end of each treatment period, including all testing time-points. Statistical analysis: Friedman test (SPSS 14.0 for Windows);

FIG. 4 shows changes in parameters of fine motor coordination upon EPO treatment. (a) Change of performance in MacQuarrie Tapping test (MacQuarrie T W. MacQuarrie Test for Mechanical Ability. Monterey, Calif.: CTB/McGraw-Hill, 1925, 1953), (b) MacQuarrie Dotting test (MacQuarrie T W. MacQuarrie Test for Mechanical Ability. Monterey, Calif.: CTB/McGraw-Hill, 1925, 1953), and (c) 9-hole peg test (Cutter G R, Baier M L, Rudick R A, Cookfair D L, Fischer J S, Petkau J, et al. Development of a multiple sclerosis functional composite as a clinical trial outcome measure. Brain 1999; 122 (Pt 5): 871-82), is expressed as % individual baseline. The mean of all available baseline values of each patient was set to 100% for each of these parameters and used for calculating individual change over time. Mean change of all patients within each group during follow-up upon treatment or during the treatment-free period is expressed in % baseline. Low-dose EPO MS patients and Parkinson patients were only followed until week 12. Filled circles: high-dose EPO MS patients (N=5); open circles: low-dose EPO MS patients (N=3); gray triangles: high-dose EPO Parkinson patients (N=2). Significance values refer to the high-dose EPO MS patients only and denote changes of the respective parameter from baseline to the end of each treatment period, including all testing time-points. Statistical analysis: Friedman test; and FIG. 5 shows changes in cognitive function tests upon EPO treatment. (a) Decrease of reaction time in Trail Making—Part B. (b) Improvement of performance on WMS-R Letter Number Sequencing. (c-d) Reduction of reaction time in TAP subtests Visual Scanning—critical trials and Working Memory in the high-dose EPO MS group (N=5). Low-dose EPO MS and Parkinson patients fail to show improvement. The mean of two baseline values of each patient was set to 100% for each of the cognitive parameters and used for calculating individual change over time. Mean change of all patients within each group during follow-up upon treatment or during the treatment-free period is expressed in % baseline. Low-dose EPO MS patients and Parkinson patients were only followed until week 12. Filled circles: high-dose EPO MS patients (N=5); open circles: low-dose EPO MS patients (N=3); gray triangles: high-dose EPO Parkinson patients (N=2). Significance values refer to the high-dose EPO MS patients only and denote changes of the respective parameter from baseline to the end of each treatment period, including all testing time-points. Statistical analysis: Friedman test.

DETAILED DESCRIPTION OF THE PRESENT STUDY AND ITS RESULTS

The main objectives of the present study were: (1) to evaluate safety of long-term high-dose EPO treatment in chronic progressive MS, and (2) to collect first evidence of potential efficacy with respect to a variety of clinical parameters, in particular Expanded Disability Status Scale (EDSS), but also walking distance, fine motor function and cognition. A careful and comprehensive individual follow-up of a small number of patients during a 6-week lead-in phase, a 12-24 week treatment phase, and a 24-week post-treatment phase delivered information about dosing of EPO, necessary duration of treatment in order to see improvement, and effect of EPO treatment-free periods on maintaining status. Finally, effects found in chronic progressive MS could be compared to effects observed in drug-naïve patients suffering from another degenerative disease, Morbus Parkinson.

Materials and Methods

Patients and Procedures

Following announcement of the present exploratory study to the local ethical committee, a total of eight patients suffering from chronic progressive MS (primary or secondary), who had previously failed on disease-modifying drugs, and, as disease control, two patients with Morbus Parkinson were included into this study (for overview see Table 1). Written informed consent was obtained after comprehensive and repeated information of the respective patient in the absence and in the presence of selected relatives or close advisors (mostly physicians). Patients were fully aware that they participated in an experimental study, set up to evaluate safety and efficacy of EPO in chronic progressive MS with respect to EDSS score. The study was designed as an exploratory open-label study employing two different doses of recombinant human (rh) EPO. The high dose (48000 IU of EPOα, ERYPO$^R$, Janssen-Cilag, Germany) was selected as presumably effective dose, based on previous trials in stroke and in schizophrenia patients, whereas the low dose (8000 IU of EPOα) lies in the upper dose range of anemia treatment (e.g. Eschbach J W, Egrie J C, Downing M R, Browne J K, Adamson J W. Correction of the anemia of end-stage renal disease with recombinant human erythropoietin. Results of a combined phase I and II clinical trial. N Engl J Med 1987; 316: 73-8) and was explored for the first time in a neurological indication. Of the eight MS patients, five received high-dose rhEPO, whereas three received low-dose rhEPO. Dosing was randomly assigned. Patients were unaware of the dose being "high" or "low". The two drug-naïve Parkinson patients received high-dose rhEPO (48000 IU of EPOα).

An overview of the study design including tests and follow-up parameters is presented in FIG. 1. After baseline examination and confirmation of inclusion/exclusion criteria, patients entered a lead-in phase of six weeks duration, where they were asked to regularly score or test their performance in a number of items, either specifically reflecting their individual handicaps or important for general well-being and health. For that, every patient received an individually tailored questionnaire, which should provide insight into the longitudinally evaluated baseline performance as well as, later, the treatment and post-treatment follow-up period.

Following the lead-in period, the treatment period was initiated. It started with a one-week inpatient setting, which allowed a comprehensive examination of the patient including magnetic resonance tomography (MRI) of brain and spinal cord, neurological, neuropsychological, electrophysiological, urological, ophthalmological examination, and routine laboratory analyses (including EPO-antibody testing). Patients were then started on high-dose prednisolone (1000 mg/100 ml over 30 min intravenously) in order to create a comparable immunosuppression as a starting point of neuroprotective therapy. One day later, a second infusion of prednisolone was given, followed by the first infusion of EPO (48000 or 8000 IU of EPOα, respectively, in 50 ml of 0.9% sodium chloride over 15 min intravenously). The third treatment day included prednisolone followed by EPO. Parkinson patients did not receive prednisolone, but were otherwise treated identically. One day later, patients were discharged and asked to return weekly to the clinic for application of the study drug, documentation of clinical state, performance rating, monitoring of adverse events and safety, including measurement of blood pressure and routine laboratory workup. Blood letting (350-450 ml) was performed if the hematocrit exceeded 50% in male or 48% in female patients on two consecutive weeks. During the one-week inpatient phase, the 12-24 week outpatient treatment phase, as well as the 24-week post-treatment phase, patients were asked to continue regular (daily/weekly) self-rating using their individually tailored questionnaire.

Neuropsychological baseline and follow-up testing of patients included the Mehrfachwahl-Wortschatz-Intelligenztest (Lehrl S. Mehrfachwahl-Wortschatz-Intelligenztest. MWT-B. Erlangen: Straube, 1999), four subtests (Information, Similarities, Picture Completion, Block Design) of the revised German version of the Wechsler Adult Intelligence Scale (Tewes U. Hamburg-Wechsler Intelligenztest für Erwachsene. Revision 1991. Bern: Huber, 1991), the Repeatable Battery for the Assessment of Neuropsychological Status (Randolph C. RBANS Manual—Repeatable Battery for the Assessment of Neuropsychological Status. Harcourt, Tex.: Psychological Corporation, 1998), subtests Visual Scanning, Working Memory and Alertness of the computer-assisted battery for attention testing (Zimmermann P, Fimm B. Testbatterie zur Aufmerksamkeitsprüfung (TAP). Herzogenrath: PsyTest, 1995), subtest Letter Number Sequencing of the Wechsler Memory Scale—Revised (Wechsler D. Wechsler Memory Scale—3rd edition (WMS-III). Harcourt, Tex.: Psychological Corporation, 1998), Wisconsin Card Sorting Test—64 Card Version (Kongs S K, Thompson L L, Iverson G L, Heaton R K. WCST-64: Wisconsin Card Sorting Test—64 Card Version. Odessa, Fla.: Psychological Assessment Resources, 2000) and the Trail Making Test (Reitan R M. Validity of the Trail Making test as an indicator of organic brain damage. Percept Motor Skills 1958; 8: 271-276).

MRI of brain and spinal cord was conducted on a Siemens 1.5T scanner (scans before and after gadolinium; for cranial imaging transverse, coronal and sagittal T1-weighted sequences, T2-weighted TSE- and TIRM-sequences; for spinal imaging sagittal and transverse T1-weighted TIRM- and TSE-sequences, T2-weighted TSE-sequences; slice thickness: 6 mm (19 slices, cranial), 3 mm (15 slices, cervical); 4 mm (11 slices, thoracic); semi-automated volumetrical analyses carried out, in a blinded fashion, with Centricity Radiology RA 1000, General Electrics, in T2-weighted images). Electrophysiology wherever technically possible (motor-evoked potentials: MEP), maximum walking distance, fine motor assessment using the 9-hole peg test (Cutter G R, Baier M L, Rudick R A, Cookfair D L, Fischer J S, Petkau J, et al. Development of a multiple sclerosis functional composite as a clinical trial outcome measure. Brain 1999; 122 (Pt 5): 871-82; Rudick R A, Cutter G, Baier M, Fisher E, Dougherty D, Weinstock-Guttman B, et al. Use of the Multiple Sclerosis Functional Composite to predict disability in relapsing MS. Neurology 2001; 56: 1324-30), as well as MacQuarrie Tapping and Dotting tests (MacQuarrie T W. MacQuarrie Test for Mechanical Ability. Monterey, Calif.: CTB/McGraw-Hill, 1925, 1953) were performed.

Inclusion and Exclusion Criteria

An overview of all eight MS patients and the two Parkinson patients is provided in Table 1. MS patients were in a chronic progressive state (either primary or secondary) of their disease. They were free of other severe psychiatric or neurological disorders. A minimum of measurable walking distance was required. Patients were not allowed to smoke or to take sex steroid hormones to avoid a potential additional vascular risk on top of their relative immobility. Two patients quit smoking several weeks before the lead-in phase, another patient stopped taking sex steroid medication (in accordance with her gynecologist). All medication was documented. Start of any MS-related novel medication during the study was not allowed nor was any kind of iron substitution. Previous medication in all MS patients included corticosteroids, intrathecal prednisolone, beta interferon, copaxone, mitoxantrone, cyclophosphamide, iv-immunoglobulins, deoxyspergualin and riluzole. Treatment was terminated at least half a year before EPO treatment due to lack of efficacy. All patients had shown distinct progression of their disease in the past year.

"Consilium": Decision on Study Continuation after 12 Weeks

After 12 weeks of weekly EPO treatment a so-called consilium took place, integrating all test results and observations of all participating parties, the patient, potential relatives or family members, an independent MS specialist, members of the clinical neuroscience team, a clinical neurophysiologist, a neuroradiologist, and a physiotherapist. Continuation of treatment was only recommended if a patient had clearly improved performance in at least three independent items, previously identified to be affected in this particular individual, e.g. walking distance, cognition, and bladder function.

Statistical Analysis

All numerical results are presented as mean±SD. For analysis, individual mean baseline performance in each of the items of interest was set to 100% in order to reach comparable baseline values among patients. Individual change during follow-up upon treatment or during the treatment-free period was expressed in % individual baseline. This way, patients can be compared and intra-group comparisons investigating the course of various variables in the high-dose EPO MS group, including all testing time-points from baseline on, can be performed using the Friedman test of SPSS 14.0 for Windows. This special nonparametric procedure for comparing repeated measures data with small sample sizes can be used for metric as well as ordered categorical data. Supplementary Tables 2 and 3 additionally provide significance values based on analyses of raw scores. Inter- and intragroup comparisons of MRI data were carried out using the nonparametric Mann-Whitney-U-test (independent and dependant). Statistical significance was set to 0.05 for all analyses.

Results

Study Participation

All ten patients participated in the study until the consilium took place after 12 weeks of weekly EPO treatment. At that time-point, only the five high-dose MS patients met criteria for continuation, whereas all three low-dose EPO MS patients as well as the two high-dose EPO Parkinson patients did not show sufficient improvement that would have justified continuation according to our consilium criteria for beneficial treatment response. This, however, does not prejudice effectiveness of EPO treatment with low-doses. The five high-dose EPO MS patients stayed on continuous treatment for another 12 weeks to receive intravenous high-dose EPO now once every other week. After this second treatment period, there was a 24-week treatment-free follow-up period for all high-dose EPO MS patients. One of these patients could be followed over another EPO treatment cycle.

Safety

There were no adverse events reported or observed in any of the patients at any time. One Parkinson patient complained about being tired for approximately two to three days after each EPO infusion. All other patients (high-dose as well as low-dose EPO MS and Parkinson) reported on feeling physically stronger, less tired, more optimistic, more enduring. They did not report that their sleep was in any way affected. Quality of life self-rating during that time stayed stable (data not shown). No relapses were observed in any of the MS patients during the study period. Mean changes in blood cell counts and iron parameters during and after EPO treatment are illustrated in FIG. 2. Original data (mean±SD) of high-dose and low-dose MS patients and of Parkinson patients are presented in Supplementary Table 1. The response of hemoglobin, hematocrit, and erythrocytes to EPO in MS patients was surprisingly low. Of the high-dose EPO MS group, a total of only five blood-lettings were necessary during the whole treatment phase (three times in one patient and once in two patients; see Supplementary Table 1). In the low-dose EPO group, no blood-letting had to be performed. The two Parkinson patients responded stronger to EPO and both required blood-letting. MCV and MCH declined similarly strongly in all high-dose patients. The iron parameters showed the expected pattern, more pronounced upon high-dose and less upon low-dose EPO treatment: Distinct decrease in serum ferritin levels, paralleled by increases in serum transferrin and, particularly, in soluble transferrin receptor (FIG. 2; Supplementary Table 1). Platelet counts increased in all patients at approximately the same rate but stayed essentially within the normal range. Whereas there was no measurable change in c-reactive protein (CRP), erythrocyte sedimentation rate tended to decrease in all patients over time of EPO treatment. All patients were EPO-antibody negative at baseline and none of the patients had developed EPO-antibodies by the end of the treatment period. No appreciable change in blood pressure upon EPO treatment was observed in any of the patients (data not shown).

Motor Function

All patients in the high-dose EPO MS group showed a significant improvement in their maximum walking distance over time as compared to baseline, which became first apparent after three weeks, gradually improved during the treatment phase to reach a plateau at around eight weeks and still persisted after cessation of EPO treatment (FIG. 3a,b; Supplementary Table 2). The increase in maximum walking distance in high-dose EPO MS patients resulted in a reduction of the EDSS (FIG. 3c) and was paralleled in patients, who could be followed electrophysiologically, by a reduction in the central motor conduction time (left Tibialis MEP; FIG. 3d, Supplementary Table 2). In contrast, neither low-dose EPO MS patients nor Parkinson patients, according to the Unified Parkinson's Disease Rating Score (Movement Disorder Society Task Force on Rating Scales for Parkinson's Disease, 2003; Fahn S, Elton R L. Unified Parkinson's Disease Rating Scale. In: Fahn S, Marsden C D, Calne D B and Goldstein M, editors. Recent Developments in Parkinson's Disease. Florham Park, N.J.: Macmillan Health Care Information, 1987), displayed any measurable beneficial effect on walking distance/gait. FIG. 3b illustrates the course of the maximum walking distance, both supervised and self-measurements, over more than one year in one of the high-dose EPO MS patients who underwent two EPO treatment periods. The trend-line from lead-in to the end of the observation period clearly directs upwards, with no change after switch to bi-weekly application. The EPO treatment break did not provoke any loss of the gained function, underlining that the effect of EPO is long lasting. Also, results of supervised ratings and self-ratings were quite consistent.

Fine motor performance in MacQuarrie Tapping and Dotting tests also showed improvement in high-dose EPO MS patients only (FIG. 4a,b), whereas in the 9-hole peg test, there was no significant beneficial effect of EPO treatment in any group and no group difference (FIG. 4c; Supplementary Table 2). Medianus MEP stayed stable over time (Supplementary Table 2). Bladder function was initially reported to be affected in three of the five high-dose and all three low-dose EPO MS patients. Subjective rating by the patients yielded distinct improvement only upon high-dose EPO treatment (data not shown). One MS patient with respiratory insufficiency due to muscle weakness showed improvement in lung function (vital capacity and forced vital capacity) upon high-dose EPO treatment.

Cognitive Functions

Premorbid intelligence as measured at baseline with the MWT-B was almost identical in all MS patients (Table 1). In contrast, estimation of the current intelligence using HAWIE-R showed a higher variability (high-dose EPO MS: 132.8±15.4; low-dose EPO MS: 119.3±14.7). High-dose EPO MS patients displayed a clear improvement in cognitive tests related to executive functioning, i.e. Trail Making—Part B, WMS-R Letter Number Sequencing, Visual Scanning, RBANS Coding and Working Memory, and psychomotor speed (Trail Making—Part A), which was absent both in low-dose MS and Parkinson patients (FIG. 5, Supplementary Table 3). This improvement remained stable even during the EPO treatment break. In contrast, parameters of learning and memory (see Supplementary Table 3 for the most relevant items) remained essentially unchanged on a high performance level, consistent with a ceiling effect.

Other Outcome and Follow-Up Parameters

Analysis of MRI data did not uncover changes upon EPO treatment. Volumetrical analysis of total brain (excluding cerebellum, brain stem and ventricles) as well as of ventricles did not yield differences among high and low-dose MS patients upon study entry (1195.8±65.6 ml versus 1013.6±189.7 ml, p=0.4; and 48.3±17.6 ml versus 46.4±12.8 ml, p=0.857). Follow-up of the high-dose patients after three months (3.6±1.1 months) showed no change in total brain or ventricle volume compared to baseline (baseline versus 3 months: 1195.8±65.6 ml versus 1152.4±47.7 ml, p=0.317; and 48.3±17.6 ml versus 47.9±17.8 ml, p=1.0). Serum levels of the glial damage marker S100B did not reveal consistent changes in any of the patients upon treatment (Supplementary Table 1).

Conclusion

The results presented above demonstrate safety and potential beneficial effects of long-term EPO treatment in chronic progressive MS. In this study, there were no adverse events, no safety concerns, and an astonishingly low need of blood lettings. Using an intra-individual follow-up design, a significant clinical and a tendency of electrophysiological improvement of motor function in chronic progressive MS at least upon high-dose EPO treatment was found as reflected by a reduction in EDSS. Improvement of this score has to our knowledge not yet been observed in any chronic progressive MS trial.

The demonstrated beneficial effects on motor function and cognition cannot simply explained by improved mood since an improvement in general well-being and mood was observed in all patients, independent of the dose, and became evident already after the first infusion of EPO. In contrast to mood and general well-being, no clear beneficial effect of low-dose EPO treatment in MS patients on any of the other parameters tested could be demonstrated at present. Further, there was no measurable effect of high-dose EPO treatment in the two drug-naïve Parkinson patients. These latter findings may also exclude a pure placebo effect to explain the improvement found in EPO MS patients.

The improvement was kept during EPO reduction and even after complete cessation of EPO treatment over a follow-up time of 24 weeks, pointing to a regenerative effect mediated by EPO rather than a temporary and short-lived action. These results may be tested using an interval treatment as described in DE 10 2006 004 008.2 and in PCT/EP2007/000640. The teaching of this document with respect to the beneficial effects of EPO in patients suffering from multiple sclerosis using an interval treatment is fully included into the present document by reference. It remains to be determined, however, whether continuation of EPO treatment in MS patients after a treatment-free interval will lead to further improvement, or at least contribute to maintaining the improved status and to slowing of progression. The observations in one of our patients who could be followed over more than one year and two EPO treatment cycles, supports the latter assumption.

Taken together, we were able to provide first evidence that EPO may show an effect on the clinical course, as demonstrated by the EDSS score, of chronic progressive MS, acting via as yet undetermined mechanisms that improve function, enhance regeneration and/or slow deterioration. Although there are reports of beneficial effects of EPO in rodent studies of EAE, EPO is the first compound that apparently demonstrated to effect an improvement in EDSS and a tendency of improvement in central motor conduction time in a cohort of chronic progressive MS patients.

Of note is the fact that all MS patients, high-dose as well as low-dose EPO received the same three-day high-dose corticosteroid infusion to create an immunologically comparable starting-point of longterm EPO therapy. Although no persisting beneficial effects of steroid treatment per se would be expected (but rather a potential rebound effect, i.e. a relapse of the disease after discontinuation of therapy—Agnello D, Bigini P, Villa P, Mennini T. Cerami A, Brines M L, et al. Erythropoietin exerts an anti-inflammatory effect on the CNS in a model of experimental autoimmune encephalomyelitis. Brain Res 2002; 952: 128-34), the lasting clinical improvement in the high-dose EPO MS group makes a steroid effect explaining this improvement very unlikely.

Regarding the mechanism of action of EPO on motor and cognitive performance in chronic progressive MS, the observed gradual improvement, first visible after a latency of several weeks, and, in particular, its stability over several months of EPO reduction and EPO treatment-free interval, suggests a morphological rather than a purely functional and transient effect. This is further supported by the observed improvement of the central motor conduction time. This improvement is particularly striking and difficult to reconcile with the known spectrum of EPO functions, as remyelination by EPO has not yet been demonstrated.

Whereas the obvious failure of low-dose EPO to lead to an appreciable improvement in MS patients might be explained by an insufficient concentration of EPO achieved in the central nervous system, it is unclear why the Parkinson patients did not have any measurable benefit. EPO penetrates through a blood-brain-barrier at least upon high-dose peripheral application (Banks et al., 2004; Brines et al., 2000; Ehrenreich et al., 2004b; Xenocostas et al., 2005) and should therefore have reached the brain also in the two Parkinson patients in amounts sufficient to exert neurotrophic effects. In this disease, however, symptoms become usually overt when 70% of neurons in the substantia nigra are degenerated (Koller W C. When does Parkinson's disease begin? Neurology 1992; 42: 27-31; discussion 41-8). Neurotrophic effects on the remaining neuronal population may not lead to rapid clinical improvement or require longer time periods of treatment and follow-up.

The infrequent requirement of blood lettings in MS patients, consistent with a relative hyporesponsiveness of the hematopoietic system to EPO (Kwack C, Balakrishnan VS. Managing erythropoietin hyporesponsiveness. Semin Dial 2006; 19: 146-51), might be due to a systemic latent inflammatory condition altering cytokine patterns that modulate the bone marrow response to EPO. This proposed latent inflammatory condition cannot be easily diagnosed with routine laboratory parameters of inflammation. Here, the response of the hematopoietic system to EPO might even serve in future studies of MS as an indicator of occult inflammation, and thus requirement of additional immunosuppression. Moreover, the hyporesponsiveness of the hematopoietic system, in contrast to the nervous system, to EPO in MS supports the notion that the observed therapeutic efficacy in MS is not simply due to improved oxygen supply via increased red blood cell mass.

EPO treatment leads to temporary shifts in iron stores as delineated here by several determinants of iron metabolism. Accelerated and intensified integration of iron into new red blood cells and thereby withdrawal of iron from its stores, leads to a picture similar to that of true iron deficiency. This picture is corrected after termination of EPO treatment without extra iron substitution. In the absence of appreciable blood loss and upon normal nutrition, iron deficiency will not occur. Binding more and more of the freely available iron, on the other hand, might additionally reduce inflammatory processes in MS and thereby contribute to the beneficial effect of high-dose long-term EPO treatment. In fact, iron chelators have been proposed for treatment of MS (e.g. desferrioxamine; Lynch S G, Fonseca T, Levine S M. A multiple course trial of desferrioxamine in chronic progressive multiple sclerosis. Cell Mol Biol (Noisy-le-grand) 2000; 46: 865-9)). Interestingly, disturbed iron metabolism has been described in MS patients (Sfagos C, Makis A C, Chaidos A, Hatzimichael E C, Dalamaga A, Kosma K, et al. Serum ferritin, transferrin and soluble transferrin receptor levels in multiple sclerosis patients. Mult Scler 2005; 11: 272-5).

To summarize, in the presented example, eight MS patients, five randomly assigned to high-dose (48000 IU), three to low-dose (8000 IU) rhEPO treatment, and, as disease controls, two drug-naïve Parkinson patients (receiving 48000 IU) were followed over up to 48 weeks: A 6-week lead-in phase, a 12-week treatment phase with weekly EPO, another 12-week treatment phase with bi-weekly EPO, and a 24-week post-treatment phase. Not only an improvement of cognitive performance or the first time but also a reduction in EDSS was observed upon high-dose EPO treatment in MS patients, persisting for three to six months after cessation of EPO application. In contrast, low-dose EPO MS patients and drug-naïve Parkinson patients did not improve in any of the parameters tested in the present study. There were no adverse events, no safety concerns and a surprisingly low need of blood-lettings.

TABLE 1

Patient Characteristics

| Treatment group | Patient ID | Age (years) | Sex | Education total (years) | Premorbid intelligence quotient[a] | Disease duration (years) | Disease subtype | Optic nerve involvement[b] | Leading symptoms | EDSS upon inclusion | Walking distance upon inclusion |
|---|---|---|---|---|---|---|---|---|---|---|---|
| MS high-dose ((N = 5) | 1 | 34 | female | 19.5 | 118 | 9.2 | PPMS | none | tetraspastic (mainly legs/right side), slight ataxia | 5.5 | 88 m |
| | 2 | 42 | male | 22 | 112 | 9.7 | SPMS | none | ataxia, dysarthria, urinary dysfunction, mild cognitive deficits, fatigue, inadequate affect | 6.0 | 140 m (with crutch) |
| | 3 | 53 | male | 20.5 | 136 | 19.3 | PPMS | bilateral | tetraspastic (mainly legs/left side), urinary/bowel dysfunction, slight fatigue | 6.5 | 25 m (with walker) |
| | 4 | 44 | male | 20.5 | 112 | 12.1 | PPMS | bilateral | tetraspastic (mainly arms/right side), ataxia, respiratory insufficiency (muscle weakness) | 5.5 | 110 m |
| | 5 | 45 | female | 20 | 143 | 14.8 | SPMS | none | tetraspastic, ataxia of upper limbs, urinary/bowel dysfunction, fatigue, dysthymia | 6.0 | 77 m (intermittent assistance) |
| | | 43.6 (6.8) | m/f: 3/2 | 20.5 (0.9) | 124.2 (14.4) | 13.0 (4.1) | 3x PPMS 2x SPMS | | | 5.9 (0.4) | 88.0 (42.7) |
| MS low-dose (N = 3) | 6 | 38 | male | 20 | 130 | 9.5 | PPMS | unilateral | ataxia, paraparesis, severe sensory dysfunction, urinary dysfunction, slight dysarthria | 4.5 | 381 m |
| | 7 | 42 | male | 23 | 107 | 18.3 | SPMS | bilateral | tetraspastic (mainly legs), urinary dysfunction, cognitive deficits, INO, dysarthria | 6.5 | 54 m (with walker) |
| | 8 | 63 | female | 23 | 136 | 10.4 | SPMS | none | paresis (mainly legs/right side), muscle cramps, urinary dysfunction, dysarthria | 6.0 | 118 m (with cane) |
| | | 47.7 (13.4) | m/f: 2/1 | 22.0 (1.7) | 124.3 (15.3) | 12.7 (4.8) | 1x PPMS 2x SPMS | | | 5.7 (1.0) | 184.3 (173.3) |

| Treatment group | Patient ID | Age (years) | Sex | Education total (years) | Premorbid intelligence quotient* | Disease duration (years) | Disease subtype | — | Leading symptoms | UPDRS upon inclusion | — |
|---|---|---|---|---|---|---|---|---|---|---|---|
| Parkinson high-dose (N = 2) | 9 | 43 | male | 24 | 145 | 1.8 | idiopathic | — | tremor (mainly right side), rigidity, bradykinesia, micrography, mild cognitive deficits, dysarthria | 30 | — |
| | 10 | 73 | female | 18 | 118 | 0.7 | idiopathic | — | tremor (mainly legs), bradykinesia, impaired fine motor function, fatigue, cognitive dysfunction | 20 | — |

Means (SD) presented for treatment groups "MS high-dose" and "MS low-dose".
PPMS: primary progressive multiple sclerosis.
SPMS: secondary progressive multiple sclerosis.
EDSS: Expanded Disability Status Scale;
UPDRS: Unified Parkinson's Disease Rating Scale;
INO: internuclear opthalmoplegia.
[a]Premorbid intelligence quotient based on results of the Mehrfachwahl-Wortschatz-Intelligenztest (MWT-B).
[b]State of ophthalmological examination and VEPs (visual evoked potentials) upon study entry which remained unchanged during follow-up.

SUPPLEMENTARY TABLE 1

Routine Laboratory Data

| | Baseline | EPO weekly | | | | | | | | | | | |
|---|---|---|---|---|---|---|---|---|---|---|---|---|---|
| | Mean baseline Mean (SD) | Week 1 Mean (SD) | Week 2 Mean (SD) | Week 3 Mean (SD) | Week 4 Mean (SD) | Week 5 Mean (SD) | Week 6 Mean (SD) | Week 7 Mean (SD) | Week 8 Mean (SD) | Week 9 Mean (SD) | Week 10 Mean (SD) | Week 11 Mean (SD) | Week 12 Mean (SD) |
| Hemoglobin (g/dl) | | | | | | | | | | | | | |
| MS high-dose (N = 5) | 15.06 (0.87) | 13.98 (1.19) | 14.62 (0.72) | 14.90 (0.46) | 15.38 (1.05) | 15.18 (1.48) | 15.34 (0.67) | 15.34 (1.82) | 14.60 (1.65) | 14.30 (1.30) | 14.54 (0.81) | 14.70 (1.25) | 14.36 (1.15) |

TABLE 1-continued

Patient Characteristics

| | | | | | | | | | | | | | |
|---|---|---|---|---|---|---|---|---|---|---|---|---|---|
| MS low-dose | 14.22 | 14.90 | 15.00 | 14.83 | 14.57 | 15.63 | 15.00 | 15.10 | 15.23 | 15.13 | 15.50 | 15.13 | 15.67 |
| (N = 3) | (1.18) | (0.80) | (0.70) | (0.81) | (0.81) | (0.91) | (1.06) | (0.98) | (0.81) | (0.70) | (1.14) | (0.67) | (0.59) |
| Parkinson high-dose | 14.23 | 13.65 | 14.30 | 14.60 | 15.35 | 15.55 | 15.45 | 15.95 | 15.95 | 15.75 | 15.75 | 16.60 | 15.95 |
| (N = 2) | (2.93) | (1.48) | (1.70) | (0.99) | (2.33) | (2.33) | (0.64) | (1.06) | (0.49) | (0.78) | (0.78) | (1.98) | (1.34) |
| Hematacrit (%) | | | | | | | | | | | | | |
| MS high-dose | 44.82 | 41.94 | 44.60 | 45.50 | 48.38 | 46.52[1] | 47.78 | 47.04[2] | 45.72[1] | 44.72[1] | 45.26 | 45.96 | 45.14 |
| (N = 5) | (2.48) | (3.09) | (1.50) | (1.37) | (2.49) | (5.02) | (0.98) | (5.66) | (4.54) | (4.22) | (2.62) | (3.68) | (2.55) |
| MS low-dose | 42.72 | 45.47 | 44.73 | 44.73 | 43.6 | 47.23 | 44.77 | 45.80 | 45.87 | 45.70 | 46.73 | 45.97 | 48.10 |
| (N = 3) | (4.19) | (2.49) | (2.22) | (3.86) | (2.34) | (2.48) | (3.40) | (3.66) | (2.05) | (2.45) | (3.61) | (2.41) | (2.03) |
| Parkinson high-dose | 41.58 | 40.30 | 42.55 | 43.00 | 47.40 | 47.35[1] | 45.90 | 49.50 | 48.75 | 47.65 | 48.55 | 52.95[1] | 50.20[1] |
| (N = 2) | (7.60) | (3.68) | (5.30) | (3.11) | (6.93) | (6.15) | (0.28) | (4.67) | (0.78) | (2.62) | (0.49) | (6.86) | (4.38) |
| Erythrocytes (Mio/μl) | | | | | | | | | | | | | |
| MS high-dose | 5.00 | 4.64 | 4.97 | 5.04 | 5.41 | 5.20 | 5.38 | 5.37 | 5.25 | 5.22 | 5.32 | 5.46 | 5.46 |
| (N = 5) | (0.26) | (0.40) | (0.26) | (0.19) | (0.09) | (0.55) | (0.28) | (0.69) | (0.51) | (0.41) | (0.20) | (0.47) | (0.22) |
| MS low-dose | 4.78 | 5.04 | 4.87 | 4.92 | 4.82 | 5.18 | 4.92 | 5.03 | 5.06 | 5.07 | 5.20 | 5.31 | 5.33 |
| (N = 3) | (0.39) | (0.15) | (0.29) | (0.35) | (0.18) | (0.24) | (0.31) | (0.34) | (0.11) | (0.19) | (0.30) | (0.25) | (0.17) |
| Parkinson high-dose | 4.72 | 4.53 | 4.81 | 4.85 | 5.33 | 5.33 | 5.24 | 5.66 | 5.60 | 5.50 | 5.72 | 6.30 | 5.96 |
| (N = 2) | (1.11) | (0.68) | (0.83) | (0.57) | (0.97) | (0.92) | (0.26) | (0.83) | (0.16) | (0.45) | (0.27) | (0.98) | (0.77 |
| Reticulocytes (‰) | | | | | | | | | | | | | |
| MS high-dose | 13.30 | 20.60 | 29.40 | 23.40 | 15.25 | 14.80 | 11.80 | 14.00 | 13.00 | 11.20 | 11.40 | 10.00 | 7.80 |
| (N = 5) | (3.85) | (1.67) | (7.09) | (7.92) | (5.32) | (3.27) | (4.82) | (5.70) | (5.70) | (4.97) | (3.51) | (3.39) | (1.92) |
| MS low-dose | 10.00 | 19.33 | 17.00 | 12.67 | 12.67 | 12.67 | 10.67 | 10.33 | 10.67 | 10.00 | 9.33 | 7.67 | 8.00 |
| (N = 3) | (1.32) | (1.15) | (6.08) | (3.21) | (0.58) | (3.51) | (1.53) | (1.53) | (2.52) | (2.65) | (3.21) | (1.15) | (1.00) |
| Parkinson high-dose | 15.75 | 24.50 | 42.00 | 20.50 | 20.00 | 14.00 | 20.50 | 15.50 | 16.00 | 9.00 | 10.50 | 12.50 | 9.00 |
| (N = 2) | (5.30) | (2.12) | (2.83) | (2.12) | (5.66) | (0.00) | (12.0) | (0.71) | (1.41) | (5.66) | (2.12) | (2.12) | (2.83) |
| MCV (fl) | | | | | | | | | | | | | |
| MS high-dose | 89.70 | 90.60 | 90.20 | 90.20 | 89.50 | 89.60 | 88.60 | 87.80 | 87.00 | 85.74 | 84.80 | 84.20 | 82.60 |
| (N = 5) | (3.91) | (2.97) | (3.27) | (3.49) | (3.87) | (4.04) | (2.88) | (2.59) | (3.39) | (3.54) | (2.17) | (3.42) | (3.65) |
| MS low-dose | 89.50 | 90.17 | 90.33 | 91.00 | 90.67 | 91.33 | 91.00 | 91.00 | 90.33 | 90.00 | 90.00 | 90.67 | 90.33 |
| (N = 3) | (1.50) | (2.36) | (1.15) | (1.73) | (1.53) | (0.58) | (1.73) | (1.00) | (2.08) | (1.73) | (1.73) | (2.31) | (2.08) |
| Parkinson high-dose | 88.75 | 89.50 | 89.00 | 89.00 | 89.50 | 89.00 | 88.00 | 88.00 | 87.00 | 86.50 | 85.00 | 84.50 | 84.50 |
| (N = 2) | (4.60) | (4.95) | (4.24) | (4.24) | (3.54) | (4.24) | (4.24) | (4.24) | (4.24) | (2.12) | (2.83) | (2.12) | (3.54) |
| MCH (pg) | | | | | | | | | | | | | |
| MS high-dose | 30.14 | 30.14 | 29.52 | 29.52 | 29.23 | 29.22 | 28.54 | 28.68 | 27.80 | 27.42 | 27.32 | 26.94 | 26.30 |
| (N = 5) | (0.79) | (1.17) | (1.51) | (0.69) | (0.85) | (1.27) | (1.35) | (1.43) | (1.03) | (0.48) | (0.99) | (1.58) | (1.89) |
| MS low-dose | 29.70 | 29.60 | 30.17 | 30.20 | 30.20 | 30.17 | 30.47 | 30.00 | 30.10 | 29.87 | 29.87 | 29.83 | 29.40 |
| (N = 3) | (0.44) | (1.04) | (0.83) | (0.82) | (0.66) | (0.76) | (0.83) | (0.26) | (1.11) | (0.45) | (0.93) | (0.61) | (0.98) |
| Parkinson high-dose | 30.25 | 30.25 | 29.90 | 30.20 | 28.80 | 29.30 | 29.60 | 28.35 | 28.55 | 28.60 | 27.80 | 26.40 | 26.90 |
| (N = 2) | (0.92) | (1.34) | (1.56) | (1.56) | (0.85) | (0.71) | (0.28) | (2.19) | (0.07) | (0.99) | (0.42) | (0.99) | (1.27) |
| Thrombocytes (Tsd/μl) | | | | | | | | | | | | | |
| MS high-dose | 259.6 | 231.8 | 267.8 | 263.0 | 326.3 | 321.4 | 310.8 | 275.6 | 293.6 | 309.6 | 316.4 | 315.6 | 303.6 |
| (N = 5) | (19.0) | (55.8) | (25.7) | (51.8) | (75.6) | (43.6) | (41.3) | (15.7) | (23.1) | (61.8) | (23.1) | (33.3) | (40.3) |
| MS low-dose | 282.8 | 307.7 | 301.7 | 324.0 | 322.7 | 381.0 | 331.7 | 328.7 | 307.7 | 341.7 | 338.0 | 322.7 | 323.3 |
| (N = 3) | (62.6) | (54.5) | (21.5) | (57.7) | (59.0) | (46.0) | (31.6) | (40.4) | (60.6) | (41.0) | (43.5) | (48.9) | (66.5) |
| Parkinson high-dose | 245.8 | 244.0 | 277.0 | 228.0 | 250.5 | 272.5 | 294.5 | 282.0 | 275.0 | 261.0 | 290.0 | 308.5 | 292.0 |
| (N = 2) | (58.3) | (73.5) | (75.0) | (25.5) | (61.5) | (72.8) | (78.5) | (21.2) | (50.9) | (43.8) | (93.3) | (74.2) | (87.7) |
| Iron (μmol/l) | | | | | | | | | | | | | |
| MS high-dose | 23.93 | 8.60 | 8.94 | — | 29.88 | — | 12.82 | — | 10.86 | — | 10.60 | — | 9.50 |
| (N = 5) | (4.9) | (3.1) | (3.3) | | (7.6) | | (3.9) | | (4.2) | | (4.6) | | (1.4) |
| MS low-dose | 14.70 | — | 19.53 | — | 14.10 | — | 17.20 | — | 17.43 | — | 19.50 | — | 17.97 |
| (N = 3) | (2.8) | | (2.5) | | (3.6) | | (2.7) | | (6.7) | | (3.3) | | (7.5) |
| Parkinson high-dose | 23.95 | 10.75 | 10.10 | — | 17.20 | — | 13.30 | — | 12.45 | — | 12.75 | — | 9.55 |
| (N = 2) | (8.9) | (0.9) | (0.6) | | (3.0) | | (9.8) | | (6.2) | | (5.0) | | (2.5) |
| Transferrin (μmol/l) | | | | | | | | | | | | | |
| MS high-dose | 269.6 | 246.0 | 264.4 | — | 299.0 | — | 301.4 | — | 325.4 | — | 337.0 | — | 339.2 |
| (N = 5) | (44.3) | (26.8) | (28.7) | | (20.7) | | (22.4) | | (55.0) | | (25.8) | | (32.7) |
| MS low-dose | 232.0 | 255.0 | 250.3 | — | 246.7 | — | 255.7 | — | 250.7 | — | 267.3 | — | 275.3 |
| (N = 3) | (21.8) | (4.2) | (21.4) | | (3.5) | | (4.7) | | (8.5) | | (6.5) | | (30.0) |
| Parkinson high-dose | 262.0 | 251.0 | 260.5 | — | 285.0 | — | 301.0 | — | 319.0 | — | 314.5 | — | 312.5 |
| (N = 2) | (32.5) | (62.2) | (53.0) | | (55.2) | | (67.9) | | (58.0) | | (60.1) | | (24.7) |
| Transferrin saturation (%) | | | | | | | | | | | | | |
| MS high-dose | 36.07 | 13.96 | 13.30 | — | 39.82 | — | 17.31 | — | 13.68 | — | 12.72 | — | 11.25 |
| (N = 5) | (8.1) | (4.9) | (4.2) | | (10.4) | | (6.5) | | (5.9) | | (5.6) | | (2.0) |
| MS low-dose | 25.03 | 30.48 | 31.28 | — | 22.72 | — | 26.82 | — | 27.61 | — | 26.94 | — | 25.43 |
| (N = 3) | (3.0) | (10.2) | (5.6) | | (5.6) | | (4.5) | | (10.4) | | (3.7) | | (7.7) |
| Parkinson high-dose | 37.74 | 17.40 | 15.67 | — | 24.07 | — | 16.56 | — | 16.51 | — | 17.06 | — | 12.33 |
| (N = 2) | (18.5) | (2.9) | (2.3) | | (0.5) | | (9.2) | | (10.7) | | (9.6) | | (4.1) |

TABLE 1-continued

Patient Characteristics

| Ferritin (μg/l) | | | | | | | | | | | | |
|---|---|---|---|---|---|---|---|---|---|---|---|---|
| MS high-dose | 118.6 | 97.0 | 53.0 | — | 39.0 | — | 17.4 | — | 14.6 | — | 11.0 | — | 9.4 |
| (N = 5) | (55.9) | (53.4) | (28.5) | | (17.1) | | (8.1) | | (9.6) | | (3.0) | | (2.5) |
| MS low-dose | 162.3 | 146.0 | 126.7 | — | 84.3 | — | 75.3 | — | 79.7 | — | 56.7 | — | 54.7 |
| (N = 3) | (88.3) | (83.4) | (76.9) | | (56.3) | | (47.4) | | (70.9) | | (41.1) | | (35.1) |
| Parkinson high-dose | 177.8 | 159.0 | 77.5 | — | 42.5 | — | 20.5 | — | 13.5 | — | 14.0 | — | 12.0 |
| (N = 2) | (7.4) | (0.0) | (10.6) | | (2.1) | | (4.9) | | (2.1) | | (0.0) | | (1.4) |

Soluble transferrin receptor (mg/l)

| MS high-dose | 3.36 | 6.54 | — | — | — | — | 11.01 | — | — | — | — | — | 11.41 |
|---|---|---|---|---|---|---|---|---|---|---|---|---|---|
| (N = 5) | (0.59) | (2.11) | | | | | (2.48) | | | | | | (2.59) |
| MS low-dose | 2.29 | 3.66 | — | — | — | — | 4.02 | — | 4.17 | — | — | — | 4.11 |
| (N = 3) | (0.14) | (0.74) | | | | | (0.56) | | (0.79) | | | | (1.16) |
| Parkinson high-dose | 2.60 | — | 6.73 | — | 9.94 | — | — | — | 9.95 | — | — | — | 11.09 |
| (N = 2) | (0.82) | | (2.47) | | (1.32) | | | | (0.42) | | | | (1.19) |

CRP (mg/l)

| MS high-dose | 2.15 | 2.12 | 6.76 | — | 2.33 | — | 2.00 | — | 2.34 | — | 2.00 | — | 2.14 |
|---|---|---|---|---|---|---|---|---|---|---|---|---|---|
| (N = 5) | (0.34) | (0.27) | (8.63) | | (0.47) | | (0.00) | | (0.56) | | (0.00) | | (0.31) |
| MS low-dose | 3.83 | 2.95 | 4.73 | — | 6.70 | — | 4.27 | — | 16.93 | — | 2.80 | — | 3.33 |
| (N = 3) | (2.63) | (1.34) | (4.73) | | (7.54) | | (3.93) | | (25.9) | | (1.39) | | (2.31) |
| Parkinson high-dose | 2.00 | 2.50 | 2.55 | — | 2.00 | — | 2.00 | — | 2.00 | — | 2.00 | — | 2.00 |
| (N = 2) | (0.00) | (0.71) | (0.78) | | (0.00) | | (0.00) | | (0.00) | | (0.00) | | (0.00) |

Erythrocyte sedimentation rate (mm/1 h)

| MS high-dose | 5.50 | — | 6.75 | — | 3.60 | 2.40 | 2.80 | 2.20 | 6.80 | 3.75 | 2.60 | 4.00 | 1.67 |
|---|---|---|---|---|---|---|---|---|---|---|---|---|---|
| (N = 5) | (2.68) | | (8.02) | | (2.07) | (1.52) | (1.79) | (1.64) | (7.26) | (5.50) | (1.82) | (5.20) | (1.15) |
| MS low-dose | 9.83 | — | 5.00 | — | 2.50 | 2.00 | 6.67 | 6.67 | 7.67 | 7.33 | 4.33 | 6.33 | 5.00 |
| (N = 3) | (7.08) | | (5.29) | | (2.12) | (1.00) | (3.79) | (2.08) | (8.96) | (4.16) | (2.31) | (6.81) | (4.36) |
| Parkinson low-dose | 12.00 | — | 10.50 | — | 17.00 | 5.00 | 2.00 | 3.50 | 3.00 | 1.50 | 4.50 | 3.50 | 3.00 |
| (N = 2) | (9.19) | | (7.78) | | (22.6) | (4.24) | (1.41) | (2.12) | (2.83) | (0.71) | (0.71) | (0.71) | (2.83) |

S100B (μg/l)

| MS high-dose | 0.07 | 0.06 | 0.05 | 0.06 | 0.07 | 0.08 | 0.07 | 0.07 | 0.07 | 0.07 | 0.06 | 0.07 | 0.07 |
|---|---|---|---|---|---|---|---|---|---|---|---|---|---|
| (N = 5) | (0.04) | (0.02) | (0.03) | (0.05) | (0.05) | (0.04) | (0.04) | (0.04) | (0.03) | (0.02) | (0.04) | (0.03) | (0.03) |
| MS low-dose | 0.06 | — | 0.05 | 0.06 | 0.07 | 0.06 | 0.06 | 0.07 | 0.05 | 0.06 | 0.06 | 0.05 | 0.04 |
| (N = 3) | (0.01) | | (0.01) | (0.02) | (0.02) | (0.01) | (0.02) | (0.02) | (0.04) | (0.02) | (0.01) | (0.02) | (0.02) |
| Parkinson low-dose | 0.08 | 0.08 | 0.08 | 0.09 | 0.11 | 0.07 | 0.06 | 0.10 | 0.07 | 0.10 | 0.07 | 0.09 | 0.08 |
| (N = 2) | (0.00) | (0.00) | (0.02) | (0.03) | (0.01) | (0.01) | (0.01) | (0.04) | (0.02) | (0.02) | (0.00) | (0.04) | (0.02) |

| | EPO bi-weekly | | | | | | EPO-free period | |
|---|---|---|---|---|---|---|---|---|
| | Week 14 Mean (SD) | Week 16 Mean (SD) | Week 18 Mean (SD) | Week 20 Mean (SD) | Week 22 Mean (SD) | Week 24 Mean (SD) | Week 36 Mean (SD) | Ref. Range |
| Hemoglobin (g/dl) | | | | | | | | |
| MS high-dose (N = 5) | 14.06 (1.22) | 14.16 (1.26) | 13.96 (1.50) | 14.14 (1.53) | 13.98 (1.15) | 13.43 (0.94) | 13.98 (0.67) | male 13.5-17.5 |
| MS low-dose (N = 3) | — | — | — | — | — | — | — | female 11.5-15.0 |
| Parkinson high-dose (N = 2) | — | — | — | — | — | — | — | |
| Hematacrit (%) | | | | | | | | |
| MS high-dose (N = 5) | 44.10 (3.12) | 44.96 (3.97) | 44.24 (4.28) | 45.24 (5.12) | 44.18 (3.30) | 42.65 (3.19) | 42.16 (1.84) | male 39-51 |
| MS low-dose (N = 3) | — | — | — | — | — | — | — | female 35-46 |
| Parkinson high-dose (N = 2) | — | — | — | — | — | — | — | |
| Erythrocytes (Mio/μl) | | | | | | | | |
| MS high-dose (N = 5) | 5.44 (0.33) | 5.61 (0.41) | 5.50 (0.54) | 5.65 (0.62) | 5.48 (0.42) | 5.22 (0.40) | 4.93 (0.31) | male 4.4-5.9 |
| MS low-dose (N = 3) | — | — | — | — | — | — | — | female 3.9-5.1 |
| Parkinson high-dose (N = 2) | | | | | | | | |

TABLE 1-continued

Patient Characteristics

| Reticulocytes (‰) | | | | | | | | |
|---|---|---|---|---|---|---|---|---|
| MS high-dose (N = 5) | 6.00 (2.24) | 7.00 (3.16) | 6.00 (2.12) | 7.40 (2.70) | 8.20 (2.28) | 8.75 (2.75) | 11.60 (3.36) | <25 |
| MS low-dose (N = 3) | — | — | — | — | — | — | — | |
| Parkinson high-dose (N = 2) | — | — | — | — | — | — | — | |
| MCV (fl) | | | | | | | | |
| MS high-dose (N = 5) | 81.20 (3.27) | 80.20 (3.11) | 80.60 (2.30) | 80.20 (2.68) | 80.80 (2.59) | 81.75 (2.22) | 85.60 (2.61) | 81-95 |
| MS low-dose (N = 3) | — | — | — | — | — | — | — | |
| Parkinson high-dose (N = 2) | — | — | — | — | — | — | — | |
| MCH (pg) | | | | | | | | |
| MS high-dose (N = 5) | 25.88 (1.50) | 25.30 (1.29) | 25.40 (1.59) | 25.04 (1.03) | 25.58 (1.10) | 25.75 (0.95) | 28.34 (0.70) | 26-32 |
| MS low-dose (N = 3) | — | — | — | — | — | — | — | |
| Parkinson high-dose (N = 2) | — | — | — | — | — | — | — | |
| Thrombocytes (Tsd/μl) | | | | | | | | |
| MS high-dose (N = 5) | 273.2 (40.6) | 281.4 (33.5) | 255.4 (52.9) | 270.4 (34.9) | 285.0 (51.3) | 287.3 (21.3) | 254.4 (42.8) | 150-350 |
| MS low-dose (N = 3) | — | — | — | — | — | — | — | |
| Parkinson high-dose (N = 2) | — | — | — | — | — | — | — | |
| Iron (μmol/l) | | | | | | | | |
| MS high-dose (N = 5) | 30.08 (17.3) | 25.92 (2.5) | 30.38 (7.1) | 34.74 (18.7) | 24.90 (6.7) | 28.63 (5.7) | 21.92 (8.4) | male 12-31 female 9-30 |
| MS low-dose (N = 3) | — | — | — | — | — | — | — | |
| Parkinson high-dose (N = 2) | — | — | — | — | — | — | — | |
| Transferrin (μmol/l) | | | | | | | | |
| MS high-dose (N = 5) | 333.2 (30.8) | 327.4 (34.5) | 310.8 (43.4) | 321.8 (39.3) | 310.6 (15.9) | 305.3 (35.7) | 292.6 (25.2) | 168-336 |
| MS low-dose (N = 3) | — | — | — | — | — | — | — | |
| Parkinson high-dose (N = 2) | — | — | — | — | — | — | — | |
| Transferrin saturation (%) | | | | | | | | |
| MS high-dose (N = 5) | 35.43 (19.9) | 31.83 (4.9) | 40.22 (13.2) | 43.14 (23.9) | 31.97 (8.6) | 36.68 (3.3) | 30.66 (14.8) | 16-45 |
| MS low-dose (N = 3) | — | — | — | — | — | — | — | |
| Parkinson high-dose (N = 2) | — | — | — | — | — | — | — | |
| Ferritin (μg/l) | | | | | | | | |
| MS high-dose (N = 5) | 20.6 (9.3) | 19.4 (8.9) | 21.8 (10.0) | 29.8 (15.1) | 31.0 (15.3) | 33.5 (20.1) | 40.2 (25.0) | male 20-250 female 10-120 |
| MS low-dose (N = 3) | — | — | — | — | — | — | — | |
| Parkinson high-dose (N = 2) | — | — | — | — | — | — | — | |
| Soluble transferrin receptor (mg/l) | | | | | | | | |
| MS high-dose (N = 5) | — | 7.75 (2.18) | — | 6.70 (1.65) | — | 7.58 (0.94) | 3.80 (0.71) | male 2.2-5.0 female 1.9-4.4 |
| MS low-dose (N = 3) | — | — | — | — | — | — | — | |
| Parkinson high-dose (N = 2) | — | — | — | — | — | — | — | |
| CRP (mg/l) | | | | | | | | |
| MS high-dose (N = 5) | 2.34 (0.76) | 2.00 (0.00) | 2.06 (0.13) | 2.02 (0.04) | 3.34 (3.00) | 2.00 (0.00) | 2.60 (0.93) | <8 |

TABLE 1-continued

Patient Characteristics

| | | | | | | | | |
|---|---|---|---|---|---|---|---|---|
| MS low-dose (N = 3) | — | — | — | — | — | — | — | |
| Parkinson high-dose (N = 2) | — | — | — | — | — | — | — | |
| Erythrocyte sedimentation rate (mm/1 h) | | | | | | | | |
| MS high-dose (N = 5) | 3.60 (1.67) | 1.40 (0.55) | 2.20 (1.10) | 2.00 (1.22) | 3.20 (3.35) | 5.00 (3.37) | 5.60 (2.07) | male < 15 |
| MS low-dose (N = 3) | — | — | — | — | — | — | — | female < 20 |
| Parkinson low-dose (N = 2) | — | — | — | — | — | — | — | |
| S100B (µg/l) | | | | | | | | |
| MS high-dose (N = 5) | 0.07 (0.02) | 0.07 (0.03) | 0.07 (0.03) | 0.10 (0.03) | 0.08 (0.03) | 0.06 (0.04) | 0.09 (0.04) | <0.12 |
| MS low-dose (N = 3) | — | — | — | — | — | — | — | |
| Parkinson low-dose (N = 2) | — | — | — | — | — | — | — | |

SD = standard deviation;
ref. range = reference range of laboratory
[1,2] denotes number of blood lettings necessary in the respective week (blood letting if hematocrit >50% in male, >48% in female patients).

SUPPLEMENTARY TABLE 2

Motor Data (original) - Part 1

| | Base-line | EPO weekly | | | | | | | | | | | |
|---|---|---|---|---|---|---|---|---|---|---|---|---|---|
| | Mean baseline Mean (SD) | Week 1 Mean (SD) | Week 2 Mean (SD) | Week 3 Mean (SD) | Week 4 Mean (SD) | Week 5 Mean (SD) | Week 6 Mean (SD) | Week 7 Mean (SD) | Week 8 Mean (SD) | Week 9 Mean (SD) | Week 10 Mean (SD) | Week 11 Mean (SD) | Week 12 Mean (SD) |
| Maximum walking distance (m) | | | | | | | | | | | | | |
| MS high-dose (N = 5) | 87.9 (42.7) | 83.0 (61.2) | 99.2 (89.9) | 130.6 (61.1) | 156.2 (120.4) | 163.8 (119.0) | 134.6 (77.1) | 154.4 (120.2) | 208.4 (120.8) | 211.6 (15.0) | 200.8 (184.9) | 212.6 (220.9) | 237.4 (257.2) |
| MS low-dose (N = 3) | 184.1 (173.5) | 257.3 (292.5) | 199.7 (231.9) | 179.0 (192.0) | 162.0 (128.2) | 168.7 (152.0) | 215.3 (218.7) | 182.3 (175.6) | 204.0 (216.4) | 206.7 (174.5) | 218.0 (199.9) | 168.3 (157.7) | 199.5 (230.5) |
| 9-hole peg test - dominant hand (s) | | | | | | | | | | | | | |
| MS high-dose (N = 4*) | 30.6 (13.4) | 24.5 (6.5) | 25.6 (9.6) | 26.3 (10.6) | 24.1 (6.2) | 24.6 (8.0) | 27.0 (9.7) | 31.1 (16.5) | 27.2 (11.0) | 28.5 (16.7) | 26.0 (9.8) | 28.8 (17.4) | 30.0 (12.3) |
| MS low-dose (N = 3) | 62.6 (37.5) | 76.0 (74.8) | 53.2 (35.3) | 56.3 (33.8) | 46.3 (22.4) | 50.1 (21.1) | 48.5 (22.5) | 52.2 (28.9) | 68.5 (58.5) | 51.9 (55.4) | 46.3 (27.2) | 48.4 (24.0) | 48.4 (28.7) |
| Parkinson high-dose (N = 2) | 26.8 (1.3) | 24.8 (—) | 24.0 (2.4) | 24.8 (2.8) | 24.6 (1.2) | 24.4 (0.3) | 24.6 (2.3) | 24.5 (2.0) | 25.7 (3.1) | 23.7 (2.8) | 24.8 (1.4) | 23.1 (1.8) | 25.2 (0.60 |
| 9-hole peg test - non-dominant hand (s) | | | | | | | | | | | | | |
| MS high-dose (N = 5) | 23.4 (3.8) | 21.6 (2.7) | 21.9 (3.5) | 19.8 (2.7) | 21.0 (3.1) | 20.8 (4.0) | 22.4 (4.3) | 21.5 (3.1) | 21.6 (4.4) | 21.0 (5.0) | 20.9 (3.3) | 20.3 (4.0) | 21.4 (5.4) |
| MS low-dose (N = 3) | 31.4 (4.7) | 28.3 (4.1) | 29.8 (4.6) | 28.2 (3.6) | 29.1 (5.0) | 28.2 (3.9) | 28.0 (4.5) | 27.5 (5.2) | 29.1 (4.7) | 30.4 (5.6) | 29.0 (4.6) | 28.5 (3.8) | 32.3 (7.0) |
| Parkinson high-dose (N = 2) | 21.5 (1.5) | 18.8 (—) | 20.7 (1.8) | 20.4 (0.4) | 21.6 (1.7) | 20.1 (1.9) | 21.3 (1.3) | 21.1 (2.6) | 21.7 (3.1) | 20.8 (3.2) | 21.0 (2.6) | 20.5 (1.8) | 21.1 (4.6) |
| MacQuarrie Tapping | | | | | | | | | | | | | |
| MS high-dose (N = 5) | 34.5 (4.8) | 38.2 (6.6) | 39.8 (7.2) | — | — | — | 39.8 (7.9) | — | — | 41.6 (7.6) | — | — | 41.2 (5.9) |
| MS low-dose (N = 3) | 18.0 (7.9) | 21.0 (8.5) | 20.0 (10.8) | — | — | — | 19.0 (10.6) | — | — | 20.3 (8.7) | — | — | 20.3 (11.1) |
| Parkinson high-dose (N = 2) | 24.3 (8.1) | — | 24.5 (5.0) | — | — | — | — | — | — | — | — | — | 25.5 (12.0) |
| Mac Quarrie Dotting | | | | | | | | | | | | | |
| MS high-dose (N = 5) | 56.0 (12.5) | 59.4 (10.4) | 64.2 (6.4) | — | — | — | 66.2 (7.1) | — | — | 70.6 (12.6) | — | — | 67.0 (7.3) |

SUPPLEMENTARY TABLE 2-continued

| | | | | | | | | | | | |
|---|---|---|---|---|---|---|---|---|---|---|---|
| MS low-dose (N = 3) | 34.0 (15.3) | 36.0 (17.1) | 34.3 (21.2) | — | — | — | 34.0 (18.4) | — | — | 37.0 (18.2) | — | — | 36.7 (25.4) |
| Parkinson high-dose (N = 2) | 43.3 (10.3) | — | 40.0 (14.1) | — | — | — | — | — | — | — | — | — | 40.5 (14.9) |

| | EPO bi-weekly | | | | | | EPO-free period | | |
|---|---|---|---|---|---|---|---|---|---|
| | Week 14 Mean (SD) | Week 16 Mean (SD) | Week 18 Mean (SD) | Week 20 Mean (SD) | Week 22 Mean (SD) | Week 24 Mean (SD) | Week 36 Mean (SD) | Week 48 Mean (SD) | $P_2$ |
| Maximum walking distance (m) | | | | | | | | | |
| MS high-dose (N = 5) | 186.4 (127.5) | 202.4 (155.3) | 205.6 (172.2) | 215.6 (183.7) | 174.2 (182.4) | 193.4 (205.8) | 167.6 (160.1) | 154.2 (151.9) | 0.002 |
| MS low-dose (N = 3) | — | — | — | — | — | — | — | — | |
| 9-hole peg test - dominant hand (s) | | | | | | | | | |
| MS high-dose (N = 4*) | 25.6 (10.0) | 26.5 (10.5) | 27.8 (11.7) | 28.0 (14.7) | 26.1 (9.3) | 29.4 (14.4) | 26.8 (14.5) | — | 0.740 |
| MS low-dose (N = 3) | — | — | — | — | — | — | — | — | |
| Parkinson high-dose (N = 2) | — | — | — | — | — | — | — | — | |
| 9-hole peg test - non-dominant hand (s) | | | | | | | | | |
| MS high-dose (N = 5) | 21.3 (4.7) | 22.2 (4.2) | 21.9 (5.0) | 21.0 (4.2) | 22.2 (4.9) | 23.2 (4.5) | 21.0 (4.0) | — | 0.124 |
| MS low-dose (N = 3) | — | — | — | — | — | — | — | — | |
| Parkinson high-dose (N = 2) | — | — | — | — | — | — | — | — | |
| MacQuarrie Tapping | | | | | | | | | |
| MS high-dose (N = 5) | — | — | 42.2 (6.9) | — | — | 39.8 (10.6) | 41.6 (7.9) | — | 0.041 |
| MS low-dose (N = 3) | — | — | — | — | — | — | — | — | |
| Parkinson high-dose (N = 2) | — | — | — | — | — | — | — | — | |
| Mac Quarrie Dotting | | | | | | | | | |
| MS high-dose (N = 5) | — | — | 67.0 (6.0) | — | — | 63.6 (10.4) | 66.6 (10.0) | — | 0.057 |
| MS low-dose (N = 3) | — | — | — | — | — | — | — | — | |
| Parkinson high-dose (N = 2) | — | — | — | — | — | — | — | — | |

SD: standard deviation.
*Missing data due to complete paralysis of the dominant upper extremity in one patient.
(—) Value of only one patient available.
$P_2$ denotes significance from baseline to week 36.
Statistical analysis: Friedman test (performed in high-dose EPO MS patients only).

Motor Data (original) - Part 2

| | Base-line | EPO weekly | | | | | | | | | | | |
|---|---|---|---|---|---|---|---|---|---|---|---|---|---|
| MEP CMCT (ms) | Mean baseline Mean (SD) | Week 1 Mean (SD) | Week 2 Mean (SD) | Week 3 Mean (SD) | Week 4 Mean (SD) | Week 5 Mean (SD) | Week 6 Mean (SD) | Week 7 Mean (SD) | Week 8 Mean (SD) | Week 9 Mean (SD) | Week 10 Mean (SD) | Week 11 Mean (SD) | Week 12 Mean (SD) |
| Medianus nerve right | | | | | | | | | | | | | |
| MS high-dose (N = 5) | 13.9 (3.7) | — | — | — | — | — | — | — | — | — | — | — | 14.3 (3.5) |
| MS low-dose (N = 3) | 20.6 (2.2) | — | — | — | — | — | — | — | — | — | — | — | 16.8 (4.8) |

SUPPLEMENTARY TABLE 2-continued

| | Baseline Mean (SD) | | | | | | | | | | | | Week 12 Mean (SD) |
|---|---|---|---|---|---|---|---|---|---|---|---|---|---|
| Medianus nerve left | | | | | | | | | | | | | |
| MS high-dose (N = 5) | 13.6 (3.9) | — | — | — | — | — | — | — | — | — | — | — | 13.8 (4.7) |
| MS low-dose (N = 3) | 16.5 (6.1) | — | — | — | — | — | — | — | — | — | — | — | 14.5 (1.0) |
| Tibialis nerve right | | | | | | | | | | | | | |
| MS high-dose (N = 4*) | 36.6 (11.7) | — | — | — | — | — | — | — | — | — | — | — | 38.7 (9.1) |
| MS low-dose (N = 3) | 34.7 (5.0) | — | — | — | — | — | — | — | — | — | — | — | 32.1 (10.0) |
| Tibialis nerve left | | | | | | | | | | | | | |
| MS high-dose (N = 4*) | 42.5 (9.6) | — | — | — | — | — | — | — | — | — | — | — | 38.6 (10.1) |
| MS low-dose (N = 3) | 31.8 (10.1) | — | — | — | — | — | — | — | — | — | — | — | 30.4 (16.5) |

| MEP CMCT (ms) | EPO bi-weekly | | | | | | EPO-free period | | |
|---|---|---|---|---|---|---|---|---|---|
| | Week 14 Mean (SD) | Week 16 Mean (SD) | Week 18 Mean (SD) | Week 20 Mean (SD) | Week 22 Mean (SD) | Week 24 Mean (SD) | Week 36 Mean (SD) | Week 48 Mean (SD) | $P_1$ |
| Medianus nerve right | | | | | | | | | |
| MS high-dose (N = 5) | — | — | — | — | — | 13.8 (3.2) | — | — | 1.000 |
| MS low-dose (N = 3) | — | — | — | — | — | — | — | — | |
| Medianus nerve left | | | | | | | | | |
| MS high-dose (N = 5) | — | — | — | — | — | 14.3 (3.9) | — | — | 0.819 |
| MS low-dose (N = 3) | — | — | — | — | — | — | — | — | |
| Tibialis nerve right | | | | | | | | | |
| MS high-dose (N = 4*) | — | — | — | — | — | 30.6 (8.6) | — | — | 0.368 |
| MS low-dose (N = 3) | — | — | — | — | — | — | — | — | |
| Tibialis nerve left | | | | | | | | | |
| MS high-dose (N = 4*) | — | — | — | — | — | 30.9 (10.9) | — | — | 0.039 |
| MS low-dose (N = 3) | — | — | — | — | — | — | — | — | |

SD: standard deviation;
MEP CMCT: motor evoked potentials central motor conduction time.
*Missing data of one patient due to methodological problems during baseline measurement.
$P_1$ denotes significance from baseline to week 24.
Statistical analysis: Friedman test (performed in high-dose EPO MS patients only).

SUPPLEMENTARY TABLE 3

Neuropsychological Test Data (original) - Part 1

| Cognitive domain | Cognitive parameter | Baseline Mean (SD) | Day 6 Mean (SD) | Week 2 Mean (SD) | Week 6 Mean (SD) | Week 9 Mean (SD) | Week 12 Mean (SD) | Week 18 Mean (SD) | Week 24 Mean (SD) | $P_1$ | Week 36 Mean (SD) | $P_2$ |
|---|---|---|---|---|---|---|---|---|---|---|---|---|
| | | | | | EPO weekly | | | EPO bi-weekly | | | EPO-free period | |
| Visual scanning/attention | Visual Scanning - critical trials (median ms) | | | | | | | | | | | |
| | MS high-dose (N = 5) | 2162.4 (621.6) | 1927.4 (432.9) | 1641.3 (410.2) | 1567.1 (524.8) | 1531.0 (534.6) | 1530.9 (402.0) | 1515.2 (563.8) | 1510.6 (534.4) | 0.007 | 1605.8 (499.8) | 0.012 |
| | MS low-dose (N = 3) | 3951.0 (305.1) | 3725.0 (867.9) | 3641.0 (956.5) | 4020.0 (884.9) | 3557.3 (578.6) | 3128.7 (170.6) | — | — | | — | |
| | Parkinson high-dose (N = 2) | 3223.6 (2754.7) | — | 2788.5 (2212.5) | — | — | 3256.5 (2717.4) | — | — | | — | |
| | Visual Scanning - noncritical trials (median ms) | | | | | | | | | | | |
| | MS high-dose (N = 5) | 3664.9 (1117.5) | 3262.7 (787.7) | 2544.4 (547.4) | 2533.4 (575.0) | 2413.3 (694.7) | 2533.8 (726.8) | 2506.2 (834.6) | 2386.2 (593.9) | 0.034 | 2509.7 (750.6) | 0.042 |
| | MS low-dose (N = 3) | 6499.5 (383.6) | 6814.0 (2018.3) | 5634.2 (1136.0) | 6408.7 (1468.0) | 5557.5 (941.3) | 4965.7 (116.1) | — | — | | — | |
| | Parkinson high-dose (N = 2) | 5325.3 (4460.1) | — | 4569.5 (3085.1) | — | — | 5780.5 (5022.6) | — | — | | — | |
| Attention/ psychomotor speed | Alertness - without cue sound (median ms) | | | | | | | | | | | |
| | MS high-dose (N = 5) | 291.1 (49.5) | 257.4 (46.3) | 257.5 (45.2) | 264.7 (29.4) | 257.0 (27.1) | 255.6 (34.0) | 264.6 (42.9) | 262.9 (38.8) | 0.316 | 283.6 (50.3) | 0.183 |
| | MS low-dose (N = 3) | 321.5 (98.8) | 305.7 (111.6) | 332.8 (123.0) | 329.2 (75.5) | 320.5 (75.5) | 287.3 (62.6) | — | — | | — | |
| | Parkinson high-dose (N = 2) | 318.9 (77.3) | — | 302.0 (77.8) | — | — | 344.0 (92.6) | — | — | | — | |
| | Alertness - with cue sound (median ms) | | | | | | | | | | | |
| | MS high-dose (N = 5) | 284.9 (56.3) | 251.9 (40.6) | 256.0 (43.7) | 254.7 (36.4) | 249.1 (22.5) | 259.1 (44.0) | 266.4 (51.9) | 258.1 (47.2) | 0.142 | 278.4 (60.3) | 0.089 |
| | MS low-dose (N = 3) | 322.8 (125.6) | 279.2 (90.6) | 328.3 (111.2) | 320.2 (81.0) | 309.7 (68.3) | 278.7 (60.3) | — | — | | — | |
| | Parkinson high-dose (N = 2) | 300.0 (38.2) | — | 266.5 (24.8) | — | — | 329.0 (73.5) | — | — | | — | |
| | RBANS Coding (raw score) | | | | | | | | | | | |
| | MS high-dose (N = 5) | 51.6 (12.0) | 53.6 (14.4) | 52.4 (10.7) | 54.6 (11.4) | 57.8 (11.9) | 55.8 (9.1) | 56.4 (16.6) | 58.2 (13.1) | 0.014 | 57.8 (14.1) | 0.017 |
| | MS low-dose (N = 3) | 27.7 (9.4) | 29.0 (10.1) | 32.3 (9.8) | 33.0 (10.1) | 33.0 (14.0) | 32.7 (14.0) | — | — | | — | |
| | Parkinson high-dose (N = 2) | 38.8 (14.5) | — | 41.5 (12.0) | — | — | 33.5 (14.8) | — | — | | — | |
| | Trail Making Part A (reaction time in s) | | | | | | | | | | | |
| | MS high-dose (N = 5) | 23.8 (4.1) | 19.2 (4.5) | 23.2 (10.1) | 20.8 (6.1) | 18.6 (4.9) | 20.6 (5.4) | 18.8 (3.5) | 19.4 (4.4) | 0.053 | 18.8 (4.5) | 0.055 |

SUPPLEMENTARY TABLE 3-continued

| | Baseline Mean (SD) | Day 6 Mean (SD) | Week 2 Mean (SD) | Week 6 Mean (SD) | Week 9 Mean (SD) | Week 12 Mean (SD) |
|---|---|---|---|---|---|---|
| MS low-dose (N = 3) | 42.0 (8.0) | 55.0 (15.7) | 58.7 (39.3) | 48.3 (20.1) | 42.0 (21.5) | 52.0 (20.9) |
| Parkinson high-dose (N = 2) | 49.0 (22.6) | — | 50.5 (37.5) | — | — | 55.5 (37.5) |

RBANS: Repeatable Battery for the Assessment of Neuropsychological Status.
$P_1$ denotes significance from baseline to week 24;
$P_2$ denotes significance from baseline to week 36;
Statistical analysis: Friedman test (performed in high-dose EPO MS patients only).

Neuropsychological Test Data (original) - Part 2

| | | Baseline | EPO weekly | | | | | EPO bi-weekly | | | EPO-free period | |
|---|---|---|---|---|---|---|---|---|---|---|---|---|
| Cognitive domain | Cognitive parameter | Baseline Mean (SD) | Day 6 Mean (SD) | Week 2 Mean (SD) | Week 6 Mean (SD) | Week 9 Mean (SD) | Week 12 Mean (SD) | Week 18 Mean (SD) | Week 24 Mean (SD) | $P_1$ | Week 36 Mean (SD) | $P_2$ |
| Working memory/ executive functions | Trail Making Part B (reaction time in s) | | | | | | | | | | | |
| | MS high-dose (N = 5) | 68.4 (26.6) | 50.8 (18.7) | 57.6 (23.0) | 60.4 (29.2) | 45.2 (14.5) | 49.8 (13.9) | 45.2 (11.3) | 51.4 (18.4) | 0.009 | 46.8 (17.5) | 0.01 |
| | MS low-dose (N = 3) | 131.0 (46.4) | 129.3 (59.4) | 156.3 (118.4) | 110.7 (66.3) | 108.0 (35.6) | 173.0 (167.2) | — | — | | — | |
| | Parkinson high-dose (N = 2) | 127.3 (102.9) | — | 112.5 (79.9) | — | — | 143.5 (130.8) | — | — | | — | |
| | Working Memory (median ms) | | | | | | | | | | | |
| | MS high-dose (N = 5) | 721.8 (261.5) | 487.6 (142.5) | 610.9 (222.2) | 682.4 (275.3) | 654.5 (325.1) | 592.9 (260.5) | 504.0 (83.3) | 548.9 (170.2) | 0.051 | 570.6 (212.4) | 0.096 |
| | MS low-dose (N = 3) | 792.3 (94.2) | 703.0 (67.3) | 792.5 (339.3) | 908.0 (207.3) | 799.8 (108.7) | 892.0 (105.9) | — | — | | — | |
| | Parkinson high-dose (N = 2) | 554.1 (63.5) | — | 619.5 (215.7) | — | — | 650.5 (252.4) | — | — | | — | |
| | WMS-R Letter Number Sequencing (raw score) | | | | | | | | | | | |
| | MS high-dose (N = 5) | 12.9 (2.8) | 12.6 (2.6) | 13.2 (3.1) | 13.8 (3.6) | 14.6 (2.6) | 14.8 (2.2) | 15.6 (3.2) | 14.4 (2.9) | 0.019 | 14.4 (2.9) | 0.031 |
| | MS low-dose (N = 3) | 10.5 (1.0) | 10.3 (0.6) | 11.0 (1.0) | 12.0 (0.0) | 11.7 (1.2) | 11.0 (2.6) | — | — | | — | |
| | Parkinson high-dose (N = 2) | 12.3 (5.3) | — | 12.5 (3.5) | — | — | 13.0 (5.7) | — | — | | — | |
| | WCST-64 perseverative errors (raw score) | | | | | | | | | | | |
| | MS high-dose (N = 5) | 8.0 (7.3) | — | — | 5.9 (4.0) | — | 7.8 (7.3) | — | 4.2 (1.6) | 0.164 | — | |
| | MS low-dose (N = 3) | 6.7 (2.5) | — | — | 7.3 (4.9) | — | 8.7 (7.2) | — | — | | — | |
| | Parkinson high-dose (N = 2) | 8.5 (6.4) | — | — | — | — | 15.0 (14.1) | — | — | | — | |
| Learning and memory | RBANS list learning (raw score) | | | | | | | | | | | |
| | MS high-dose (N = 5) | 35.8 (3.3) | — | — | 33.0 (4.4) | — | 34.0 (5.0) | — | 36.3 (3.4) | 0.084 | — | |
| | MS low-dose (N = 3) | 29.0 (5.6) | — | — | 29.3 (4.0) | — | 29.3 (5.7) | — | — | | — | |

SUPPLEMENTARY TABLE 3-continued

| | | | | | | |
|---|---|---|---|---|---|---|
| Parkinson high-dose (N = 2) | 31.0 (8.5) | — | — | 34.5 (6.4) | — | — |
| RBANS list recall (raw score) | | | | | | |
| MS high-dose (N = 5) | 9.2 (0.4) | — | 8.1 (2.0) | 7.9 (2.8) | — | 9.0 (1.7) |
| MS low-dose (N = 3) | 6.0 (4.6) | — | 6.7 (2.5) | 4.7 (3.2) | — | — |
| Parkinson high-dose (N = 2) | 7.5 (0.7) | — | — | 9.5 (0.7) | — | — | 0.506 |
| RBANS figure recall (raw score) | | | | | | |
| MS high-dose (N = 5) | 17.2 (1.8) | — | 18.8 (1.8) | 19.8 (0.4) | — | 17.6 (2.3) |
| MS low-dose (N = 3) | 15.7 (4.0) | — | 15.0 (4.6) | 16.7 (5.8) | — | — |
| Parkinson high-dose (N = 2) | 19.5 (0.7) | — | — | 19.0 (1.4) | — | — | 0.153 |

RBANS: Repeatable Battery for the Assessment of Neuropsychological Status;
WCST-64: Wisconsin Card Sorting Test - 64 Card Version.
$P_1$ denotes significance from baseline to week 24;
$P_2$ denotes significance from baseline to week 36;
Statistical analysis: Friedman test (performed in high-dose EPO MS patients only).

The invention claimed is:
1. A method of improving the expanded disability status scale (EDSS) score achieved by a mammal affected by multiple sclerosis, the method comprising:
   (a) measuring the EDSS score before administration;
   (b) administering to the mammal a substance effecting increased and/or prolonged activation and/or stimulation of an erythropoietin receptor,
       wherein the substance is selected from the group consisting of erythropoietin (EPO), Epoetin α, Epoetin β, Epoetin ω, Epoetin δ, glycosylated erythropoietin, glycosylated Epoetin α, glycosylated Epoetin β, glycosylated Epoetin ω, glycosylated Epoetin δ, sialized erythropoietin, sialized Epoetin α, sialized Epoetin β, sialized Epoetin ω, sialized Epoetin δ, Darbepoetin α, Continuous Erythropoiesis Receptor Activator (CERA), an erythropoietin receptor activating antibody, an EPO fusion protein, a HIF-stabilizer, Synthetic Erythropoiese Protein, an EPO-analogue, and an EPO-mimetic;
       wherein the substance is administered in a first application period of at least two weeks followed by an application-free period that lasts 16 to 53 weeks followed by a second application period of at least two weeks; and
   (c) measuring the EDSS score after the second application period;
       wherein the EDSS score is improved after the second application period compared to the EDSS score before administration.
2. The method of claim 1, wherein the first application period, the second application period, or each of the first and second application periods lasts 12 to 48 weeks.
3. The method of claim 2, wherein the first application period, the second application period, or each of the first and second application periods lasts 24 to 28 weeks.
4. The method of claim 1, wherein the application-free period lasts 16 to 28 weeks.
5. The method of claim 1, wherein the first application period, the second application period, or each of the first and second application periods lasts 6 to 12 weeks and the application-free period lasts up to 6 months.
6. The method of claim 1, wherein the first application period, the second application period, or each of the first and second application periods comprises two periods, the substance administered weekly in a first period and the substance administered every two weeks in a subsequent second period.
7. The method of claim 6, wherein the first application period is of weekly administration of 12 weeks and biweekly administration of 12 weeks, the application-free period is 24 weeks, and the second application period is of weekly administration of 12 weeks and biweekly administration of 12 weeks.
8. The method of claim 7, wherein the multiple sclerosis is chronic progressive multiple sclerosis and wherein the substance is administered in a dose or an equivalent to a dose of 40,000 IU to 50,000 IU per week, per application, per application time, or per any combination thereof, wherein an equivalent dose leads to comparable erythropoietin levels or comparable erythropoietin receptor activating biological activity and the international unit being international units of native or recombinant erythropoietin.
9. The method of claim 1, wherein the substance is administered in a dose or in an equivalent to a dose of 1,000 IU to 200,000 IU per week, per application, per application time, or per any combination thereof, wherein an equivalent dose leads to comparable erythropoietin levels or comparable erythropoietin receptor activating biological activity and the international unit being international units of native or recombinant erythropoietin.
10. The method of claim 9, wherein the substance is administered in a dose or in an equivalent to a dose of 40,000 IU to 50,000 IU.
11. The method of claim 1, wherein the EPO fusion protein is EPO-Fc.
12. The method of claim 1, wherein the multiple sclerosis is chronic progressive multiple sclerosis.
13. The method of claim 1, wherein the administration is effected parenterally/systemically.
14. The method of claim 1, wherein the mammal is a human.
15. A method of improving the expanded disability status scale (EDSS) score achieved by a mammal affected by multiple sclerosis, the method comprising:
   (a) measuring the EDSS score before administration;
   (b) administering to the mammal a substance effecting increased and/or prolonged activation and/or stimulation of an erythropoietin receptor,
       wherein the substance is selected from the group consisting of erythropoietin (EPO), Epoetin α, Epoetin β, Epoetin ω, Epoetin δ, glycosylated erythropoietin, glycosylated Epoetin α, glycosylated Epoetin β, glycosylated Epoetin ω, glycosylated Epoetin δ, sialized erythropoietin, sialized Epoetin α, sialized Epoetin β, sialized Epoetin ω, sialized Epoetin δ, Darbepoetin α, Continuous Erythropoiesis Receptor Activator (CERA), an erythropoietin receptor activating antibody, an EPO fusion protein, a HIF-stabilizer, Synthetic Erythropoiese Protein, an EPO-analogue, and an EPO-mimetic;
       wherein the substance is administered in a first application period of at least two weeks followed by an application-free period of 16 to 28 weeks followed by a second application period of at least two weeks; and
   (c) measuring the EDSS score during the application-free period;
       wherein the EDSS score is improved and remains improved during the application-free period compared to the EDSS score before administration.
16. The method of claim 15, wherein the first application period, the second application period, or each of the first and second application periods lasts 12 to 48 weeks.
17. The method of claim 16, wherein the first application period, the second application period, or each of the first and second application periods lasts 24 to 28 weeks.
18. The method of claim 15, wherein the first application period, the second application period, or each of the first and second application periods lasts 6 to 12 weeks.
19. The method of claim 15, wherein the first application period, the second application period, or each of the first and second application periods comprises two periods, the substance administered weekly in a first period and the substance administered every two weeks in a subsequent second period.
20. The method of claim 19, wherein the first application period is of weekly administration of 12 weeks and biweekly administration of 12 weeks, the application-free period is 24 weeks, and the second application period is of weekly administration of 12 weeks and biweekly administration of 12 weeks.
21. The method of claim 20, wherein the multiple sclerosis is chronic progressive multiple sclerosis and wherein the substance is administered in a dose or an equivalent to a dose of 40,000 IU to 50,000 IU per week, per application, per application time, or per any combination thereof, wherein an equivalent dose leads to comparable erythropoietin levels or comparable erythropoietin receptor activating biological activity and the international unit being international units of native or recombinant erythropoietin.

22. The method of claim 15, wherein the substance is administered in a dose or in an equivalent to a dose of 1,000 IU to 200,000 IU per week, per application, per application time, or per any combination thereof, wherein an equivalent dose leads to comparable erythropoietin levels or comparable erythropoietin receptor activating biological activity and the international unit being international units of native or recombinant erythropoietin.

23. The method of claim 22, wherein the substance is administered in a dose or in an equivalent to a dose of 40,000 IU to 50,000 IU.

24. The method of claim 15, wherein the EPO fusion protein is EPO-Fc.

25. The method of claim 15, wherein the multiple sclerosis is chronic progressive multiple sclerosis.

26. The method of claim 15, wherein the administration is effected parenterally/systemically.

27. The method of claim 15, wherein the mammal is a human.

28. A method of improving the expanded disability status scale (EDSS) score achieved by a mammal affected by chronic progressive multiple sclerosis, the method comprising:
   (a) measuring the EDSS score before administration;
   (b) administering to the mammal a substance effecting increased and/or prolonged activation and/or stimulation of an erythropoietin receptor,
      wherein the substance is selected from the group consisting of erythropoietin (EPO), Epoetin α, Epoetin β, Epoetin ω, Epoetin δ, glycosylated erythropoietin, glycosylated Epoetin α, glycosylated Epoetin β, glycosylated Epoetin ω, glycosylated Epoetin δ, sialized erythropoietin, sialized Epoetin α, sialized Epoetin β, sialized Epoetin ω, sialized Epoetin δ, Darbepoetin α, Continuous Erythropoiesis Receptor Activator (CERA), an erythropoietin receptor activating antibody, an EPO fusion protein, a HIF-stabilizer, Synthetic Erythropoiese Protein, an EPO-analogue, and an EPO-mimetic;
   wherein the substance is administered in a first application period followed by an application-free period followed by a second application period, wherein the first application period is of weekly administration of 12 weeks and biweekly administration of 12 weeks, the application-free period is 24 weeks, and the second application period is of weekly administration of 12 weeks and biweekly administration of 12 weeks; and
   (c) measuring the EDSS score after administration;
      wherein the EDSS score is improved after administration compared to the EDSS score before administration.

29. The method of claim 28, wherein the substance is administered in a dose or in an equivalent to a dose of 40,000 IU to 50,000 IU per week, per application, per application time, or per any combination thereof, wherein an equivalent dose leads to comparable erythropoietin levels or comparable erythropoietin receptor activating biological activity and the international unit being international units of native or recombinant erythropoietin.

30. The method of claim 28, wherein the administration is effected parenterally/systemically.

31. The method of claim 28, wherein the mammal is a human.

* * * * *